US011076133B2

United States Patent

Vilsmeier et al.

(12) United States Patent
(10) Patent No.: US 11,076,133 B2
(45) Date of Patent: Jul. 27, 2021

(54) MEDICAL TRACKING SYSTEM COMPRISING TWO OR MORE COMMUNICATING SENSOR DEVICES

(71) Applicant: Brainlab AG, Munich (DE)

(72) Inventors: Stefan Vilsmeier, Munich (DE); Timo Neubauer, Grasbrunn (DE); Christian Brack, Neusass (DE); Ingmar Hook, Feldkirchen (DE)

(73) Assignee: BRAINLAB AG, Munich (DE)

( * ) Notice: Subject to any disclaimer, the term of this patent is extended or adjusted under 35 U.S.C. 154(b) by 0 days.

(21) Appl. No.: 16/110,645

(22) Filed: Aug. 23, 2018

(65) Prior Publication Data

US 2018/0367765 A1 Dec. 20, 2018

Related U.S. Application Data

(63) Continuation of application No. 14/350,460, filed as application No. PCT/EP2011/067940 on Oct. 13, 2011, now abandoned.

(51) Int. Cl.

*H04N 7/18* (2006.01)
*A61B 34/20* (2016.01)

(52) U.S. Cl.

CPC ............. *H04N 7/183* (2013.01); *A61B 34/20* (2016.02); *A61B 2034/2046* (2016.02); *A61B 2034/2055* (2016.02); *A61B 2034/2057* (2016.02)

(58) Field of Classification Search

CPC .... A61B 2034/2046; A61B 2034/2055; A61B 2034/2057; A61B 34/20; H04N 7/183

See application file for complete search history.

(56) References Cited

U.S. PATENT DOCUMENTS 6,119,033 A 9/2000 Spigelman et al.
6,161,032 A * 12/2000 Acker ...................... A61B 5/06 324/207.11
8,862,200 B2 10/2014 Sherman et al.
2001/0034530 A1* 10/2001 Malackowski ........ A61B 34/20 606/130
2002/0198451 A1* 12/2002 Carson .................. A61B 34/20 600/424

(Continued)

FOREIGN PATENT DOCUMENTS

WO 2013053397 A1 4/2013
WO 2013053398 A1 4/2013

OTHER PUBLICATIONS

European Patent Office, International Search Report and Written Opinion for International Application No. PCT/EP2011/067940 dated Aug. 23, 2012—pp. 1-8.

(Continued)

*Primary Examiner* — Farzana Hossain

(74) *Attorney, Agent, or Firm* — Tucker Ellis LLP

(57) ABSTRACT

A medical tracking system comprising at least two sensor devices which are independently maneuverable and can be positioned in a fixed position relative to targets, each sensor device comprising at least one of an orientation sensor and a position sensor for respectively determining sensor data, the system further comprising a control unit configured to receive and combine the at least two sensor data of the at least two sensor devices in order to determine a relative position between at least two of the at least two sensor devices.

32 Claims, 15 Drawing Sheets

(56) References Cited

U.S. PATENT DOCUMENTS

2004/0243148 A1 12/2004 Wasielewski
2005/0089198 A1* 4/2005 Ono .................. G06K 9/00255 382/115
2005/0197569 A1 9/2005 McCombs
2005/0245808 A1* 11/2005 Carson .................. A61B 34/20 600/407
2007/0078678 A1 4/2007 DiSilvestro et al.
2008/0095416 A1* 4/2008 Jeung .................... A61B 90/36 382/128
2008/0119726 A1 5/2008 Immerz
2008/0180537 A1 7/2008 Weinberg et al.
2010/0100081 A1 4/2010 Tuma et al.
2010/0321473 A1* 12/2010 An ...................... H04N 5/2628 348/47
2011/0208093 A1 8/2011 Gross et al.
2011/0251625 A1 10/2011 Bulitta
2011/0254922 A1 10/2011 Schaerer et al.
2011/0263971 A1 10/2011 Nikou et al.
2011/0275957 A1* 11/2011 Bhandari .............. A61B 34/20 600/595
2012/0046536 A1 2/2012 Cheung et al.
2012/0157887 A1* 6/2012 Fanson ................. A61B 90/39 600/595
2014/0225999 A1* 8/2014 Bracke .................. A61B 34/10 348/77
2014/0247336 A1 9/2014 Vilsmeier et al.

OTHER PUBLICATIONS

International Search Report for International Application No. PCT/EP2011/067935 dated Jun. 19, 2012 pp. 1-3.

International Preliminary Report on Patentability for No. PCT/EP2011/067935 dated Apr. 15, 2014 pp. 1-7.

International Preliminary Report on Patentability, PCT/EP2011/067935, dated report: Apr. 15, 2014, pp. 1-7, The International Bureau of WIPO, Switzerland.

Decision to grant a European patent pursuant to ARticle 97 (1) EPC, European patent application No. 11769880.3. Notice from EPO dated Jun. 8, 2014; EP patent No. EP2765946; pp. 1-44, European Patent Office, Netherlands.

International Search Report and Written Opinion for International Application No. PCT/EP2011/067935 dated Jun. 19, 2012 pp. 10.

Notice of Allowance for related U.S. Appl. No. 16/185,648, dated Jun. 5, 2020. 18 pages.

* cited by examiner

Sensor Device

Sensor Device

1

2

MEDICAL TRACKING SYSTEM COMPRISING TWO OR MORE COMMUNICATING SENSOR DEVICES

TECHNICAL FIELD

The present invention relates to a medical tracking system comprising at least two sensor devices which are independently maneuverable and can be positioned in a fixed position relative to targets and a method of determining relative position between two sensor devices of a medical tracking system.

BACKGROUND

For many years, medical tracking systems, which are in particular a part of a medical or navigation system, are in use which are based on a tracking device which detects the position of markers which are attached to objects to be tracked.

SUMMARY

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

With a tracking system according to the present invention, advantageously a bulky and expensive 3D camera which captures images of marker spheres arranged in a known configuration is not obligatory. Advantageously, the likelihood of obstruction of an object to be tracked by a user is reduced. This invention aims at providing an improved medical tracking system and a method of determining a relative position between two sensor devices.

According to the present invention, a medical tracking system comprises at least two sensor devices which are independently maneuverable and can be positioned in a fixed position relative to targets. Each sensor device comprises at least one of an orientation sensor and a position sensor for respectively determining sensor data. “Respectively determining” means that at least two sensor devices each determine sensor data. The system further comprises a control unit configured to receive and combine the at least two sensor data of the at least two sensor devices in order to determine a relative position between at least two of the at least two sensor devices.

A fixed position in this document means that two objects which are in a fixed position have a relative position which does not change unless this change is explicitly and intentionally initiated. A fixed position is in particular given if a force or torque above a predetermined threshold has to be applied in order to change the position. This threshold might be 10 N or 10 Nm. In particular, the position of a sensor device remains fixed relative to a target while the target is registered or two targets are moved relative to each other as explained below. A fixed position can for example be achieved by rigidly attaching one object to another. The term “position” in this document means a spatial location in up to three (in particular less than three) translational dimensions and/or an alignment in up to three (in particular less than three) rotational dimensions. The spatial location can in particular be described just by a distance (between two objects) or just by the direction of a vector (which links two objects). The alignment can in particular be described by just the relative angle of orientation (between the two objects).

The orientation sensor determines orientation sensor data which represent the orientation of the sensor device. This orientation is preferably determined relative to an in particular stationary reference, such as a ground-fixed reference system which can be based on the direction of gravity. The reference system can therefore also be referred to as an absolute reference system. An orientation sensor may comprise a gyroscope. A gyroscope is a device for determining the orientation based on the angular momentum of a spinning object.

A position sensor determines position sensor data which represent the position of an object. Preferably, this position is given relative to the position sensor and therefore relative to the sensor device. As an alternative, the position can be determined in an absolute reference system.

An optional acceleration sensor of a sensor device determines acceleration sensor data which represent the acceleration of the sensor and thus of the sensor device. By integrating the acceleration over a period of time, a movement of the sensor device can be calculated. The acceleration sensor data can be part of the sensor data provided by the sensor device.

The orientation sensor can determine the orientation sensor data in up to three rotational dimensions, the position sensor can determine the position sensor data in up to three rotational and/or up to three translational dimensions and the acceleration sensor can determine the acceleration sensor data in up to three rotational and/or up to three translational dimensions.

The control unit receives the sensor data from the sensor devices and combines the received sensor data in order to determine the relative position between the two sensor devices. If, for example, the control unit receives orientation sensor data from two sensor devices in an absolute reference system, the control unit can calculate the relative orientation between the two sensor devices.

The term “combine” means in particular that the respective sensor data, which in particular respectively are insufficient to be the sole basis for determining the relative position, of the respective sensor devices are used together to calculate the relative position. In particular, the determination (calculation) is performed by using (combining) at least first sensor data of a first sensor device and second sensor data of a second sensor device in order to determine the relative position based on sufficient sensor data.

A relative position between two objects means the position of one of the objects relative to the other object. The relative position can also be given in up to three spatial dimensions and/or in up to three rotational dimensions. The relative position can thus comprise up to six dimensions, wherein there is a parameter for each dimension. Depending on the application or workflow, the parameters of less than six dimensions may be required or desired. So if, for example, the relative position of a plane is to be determined, only two rotational dimensions and one translational dimension are required to unambiguously describe the relative position of the plane. In another example, only one or more of the rotational dimensions of the relative position are required, for example for determining, from a plurality of relative positions, the range of motion of a joint having limited degrees of freedom.

Preferably, the sensor data provided by a single sensor device is not sufficient for determining all parameters for all desired dimensions of the relative position. In other words, the sensor data of a single sensor device is not sufficient to determine the desired number of parameters of the relative position. In yet other words, the sensor data of a single sensor device describe insufficient information on the relative position. The number of parameters which can be determined from the sensor data of a single sensor device might be less than the desired number of parameters, or the determination of a parameter might require more than the information given by the sensor data of a single sensor device. However, if the sensor data of two or more sensor devices is combined, the available information (also referred to as sufficient information) is sufficient to determine all parameters for all desired dimensions of the relative position. Preferably, the available information is more than sufficient, such that the information is overdetermined. In this case, the sensor data is also understood as representing sufficient information. This can be used for increasing the quality of the determined relative position.

In one embodiment, the control unit is located in one of the sensor devices. More preferably, two or more, preferably each of the sensor devices comprises a control unit or at least a part of the control unit. In this case, calculations, such as of the relative position, can be performed locally at several or each of the sensor devices, or some parameters of the relative position are determined in one sensor device and some parameters of the relative position are determined in another sensor device. However, the control unit may also be separate from all sensor devices.

The sensor data can be transferred wirelessly from a sensor device to a control unit, for example using a Bluetooth connection, a WLAN connection or any other suitable, preferably low-range data connection. If a control unit is comprised in a sensor device, the control unit can thus receive the sensor data from the other sensor device(s) wirelessly. The connection between sensors and the control unit within the same sensor device is preferably a wired connection.

According to a preferred implementation of the present invention, two or more sensor devices can communicate with each other. The sensor data of the communicating sensor devices are preferably jointly analyzed to determine the relative position between two (or more) sensor devices. This is particularly useful if the sensor data of a single one of the at least two sensor devices is not sufficient for determining the relative position.

A sensor device can be positioned in fixed position relative to the target, for example by rigidly attaching the sensor device to a target. A target can be an anatomical structure of a patient such as a bone, a medical instrument such as a cutting block or a pointer, or a part of the infrastructure in an operating room such as an operating table.

In an embodiment of the present invention, at least one marker is attached to at least one of the sensor devices. With the at least one marker, and preferably a plurality of markers making up a marker device, the position sensor of a sensor device can easily detect the position of the sensor device carrying the marker.

It is the function of a marker to be detected by a marker detection device (for example, a camera or an ultrasound receiver), such that its spatial position (i.e. its spatial location and/or alignment) can be ascertained. The detection device is in particular part of a navigation system. The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A marker device can for example be a reference star or a pointer or one or more (individual) markers in a predetermined spatial relationship. A marker device comprises one, two, three or more markers in a predetermined spatial relationship. This predetermined spatial relationship is in particular known to the navigation or tracking system and for example stored in a computer of the navigation or tracking system.

In one embodiment, at least one of the sensor devices comprises an orientation sensor and the control unit is configured to convert orientation data of an orientation sensor into a coordinate system determined by a target to which one of the sensor devices is attached. As an example, the target is a bone and the coordinate system is defined by the bone, for example by the transversal, longitudinal and sagittal axis. In an exemplary implementation, two sensor devices, each comprising an orientation sensor, are rigidly attached to two adjoining bones which are connected via a joint. The orientation sensor data received from the first sensor device is then converted into orientation data in a coordinate system corresponding to the bone to which the second sensor device is attached. In another exemplary implementation, one sensor device is attached to a cutting slot of an adjustable cutting block, the base of the adjustable cutting block being rigidly attached to a bone. The second sensor device is rigidly attached to the bone. The orientation sensor data of the first sensor device is then converted into orientation sensor data given in a coordinate system defined by the bone.

A position sensor may comprise a still or video camera, in particular a camera capturing a 2D or 3D image. By identifying markers in the output image of the camera, in particular by applying the laws of perspective projection of objects, the position of the markers and therefore of a target to which the markers are attached can be determined. In particular, the known size of the markers and the effect that objects in the distance appear smaller than objects close by is used to determine the distance. As an option, a position sensor may comprise a distance sensor for determining the distance of an object. The data of the distance sensor and a camera can be combined, in particular to support the calculation of the distance from the camera image. A distortion of a known shape of the marker in the image of the camera can be used to determine the relative orientation using the laws of perspective projection.

In one embodiment, the distance sensor comprises a laser beam source, wherein the laser beam generated by the laser beam source is angled compared to the optical axis of the camera. This means that the distance of the laser beam spot on the object reflecting the laser beam from the optical axis changes in the output image of the camera with the distance of the object from the camera. Preferably, the orientation of the object reflecting the laser beam is used when the distance is calculated because a tilt of this object relative to the optical axis changes the distance of the laser beam spot from the optical axis, while the distance is not changed. If the object is a sensor device, then preferably the orientation sensor of the sensor device is used to determine the orientation, and therefore the tilt, of the sensor device.

Preferably, the medical tracking system further comprises at least one display device, in particular for displaying the relative position between two sensor devices. Further preferably, the display device is located in a sensor device.

In a preferred embodiment, a sensor device comprises an orientation sensor and a position sensor. The sensor device can then be used in a plurality of tracking applications.

It is possible to use off-the-shelf (consumer) devices as sensor devices, such as an iPod touch or an iPhone provided by Apple Inc.

In one embodiment, a position sensor is a marker device detector, at least one sensor device comprises a marker device and the control unit is configured to select the function of the sensor device as either acting as a marker device detector or as a marker device in a step of the medical navigation workflow.

The present invention further relates to a method of determining a relative position between two sensor devices of a medical tracking system. The sensor devices are independently maneuverable and can be positioned in a fixed position relative to targets. The method comprises determining sensor data comprising at least one of orientation data and position data with two or more of the sensor devices. The method further comprises the step of transferring the sensor data to a control unit and determining the relative position between two sensor devices by the control unit by combining the sensor data.

The sensor data is in particular determined relative to a reference, which is also referred to as a relative position reference. This reference is preferably common to the sensor data provided by the sensor devices. For example, orientation data represents the orientation of a sensor device in an in particular absolute, ground-fixed reference system. The reference might be a field of force, and may in particular be defined by the direction of gravity and/or a magnetic field such as the field between the magnet north and south poles of the earth. By combining the orientation data of two sensor devices, the control unit can determine the relative position between the two sensor devices. The reference can also be an object. Position data may represent the relative position of a sensor device relative to the reference, such as a (in particular static) reference object like a marker or a marker device. The reference object is distinct to the at least two sensor devices and can be detected by the position sensors of the at least two sensor devices. With position data representing the relative positions of two sensor devices to a reference object being known to the control unit, the control unit can calculate the relative position between the two sensor devices.

However, the position data provided by a sensor device can also be used to determine the position of a marker or a marker device in a reference system of the sensor device. For example, the position of a marker device of a pointer can be determined relative to the sensor device, for example for registering an object to which the sensor device is attached.

In addition or as an alternative, the sensor data might comprise acceleration data representing the acceleration of a sensor device. By integrating the acceleration over a period of time, a movement of the sensor device can be calculated. This movement might be used for determining the relative position between two sensor devices.

In a preferred embodiment, each sensor device is attached to a target, such as an anatomical structure like a bone, a medical instrument or a part of an operation room infrastructure, and the relative position of the targets is determined from the relative position of the sensor devices. The sensor device might also be integrated into a medical instrument or a part of the operation room infrastructure In one embodiment, a sensor device comprising a marker device and a position sensor being a marker device detector is used as a marker device detector in one step of the medical navigation workflow for obtaining information for determining the position of a marker device and the same sensor device is used as a marker device in another step of the medical navigation workflow.

If the relative position between two sensor devices is determined repeatedly over time, the relative movement between two sensor devices can be tracked.

The present invention further relates to a method for determining a mechanical property of a joint between two bones, comprising the steps of:

positioning a first sensor device in a fixed position relative to the first bone, registering the first bone by sampling a plurality of sample points using a pointer and the first sensor device, positioning a second sensor device in a fixed position relative to the second bone, registering the second bone by sampling a plurality of sample points using a pointer and the second sensor device, optionally re-positioning the first sensor device in its fixed position relative to the first bone if the first sensor device was used as a marker device of the pointer in the previous step, determining at least one relative position between the first sensor device and the second sensor device for at least one position of the joint as described above and determining the mechanical property of the joint between the first bone and the second bone from the at least one relative position between the first sensor device and the second sensor device.

The pointer used for registering the first bone may use the second sensor device as a marker device. The pointer used for registering the second bone may use the first sensor device as a marker device. If the second bone is a bone acting together with a ball joint, such as the femur or the humerus, then an additional sample point used for registering the bone can be the center of the head of the bone. This center is determined by positioning the first sensor device in a fixed position relative to the hone forming the other part of the ball joint. The bone is then pivoted about the ball joint, wherein the second sensor device determines the relative positions of the first sensor device for a plurality of positions of the bone. Since the second sensor device moves on a spherical shell centered about the center of the head of the bone to be registered, the center of the head can be calculated.

The mechanical property of the joint is for example the range of motion, such as the range between full flexion and full extension, or a lateral tilt between the bones, such as the varus/valgus angle.

The present invention further relates to a method for aiding the adjustment an adjustable cutting block comprising a base and a cutting slot which is adjustable relative to the base, the base being attached to a bone, comprising the steps of positioning a first sensor device in a fixed position relative to the cutting slot, registering the bone by sampling a plurality of sample points using a pointer and the first sensor device such that the initial alignment of the cutting slot relative to the bone is known, positioning a second sensor device in a fixed position relative to the base of the cutting block, determining the relative position between the first sensor device and the second sensor device as described above for the initial alignment of the cutting slot, determining the relative position between the first sensor device and the second sensor device as described above while the cutting slot is adjusted and determining the current alignment of the cutting slot from the initial alignment of the cutting slot and the current relative position between the first sensor device and the second sensor device.

The pointer used for registering the bone may use the one of the sensor devices as a marker device. If the bone is a bone acting together with a ball joint, such as the femur or the humerus, then an additional sample point used for registering the bone can be the center of the head of the bone. This center is determined by positioning the second sensor device in a fixed position relative to the bone forming the other part of the ball joint. The bone is then pivoted about the ball joint, wherein the first sensor device determines the relative positions of the second sensor device for a plurality of positions of the bone. Since the first sensor device moves on a spherical shell centered about the center of the head of the bone to be registered, the center of the head can be calculated.

The current alignment of the cutting slot can be continuously compared to a desired alignment, which might be pre-planned using a 3D scan of the bone and/or the mechanical property of the bone which is determined as explained above.

After the cut has been performed using the cutting block, the cutting surface can be verified by placing a defined surface of the second sensor device on the cutting surface. Then the relative position between the first and second sensor device is determined and the alignment of the cutting surface relative to the bone can be validated.

As an option, the at least two sensor devices are brought into a known relative position between each other, for example by bringing them in contact, and the at least two sensor devices are preferably notified about this fact, for example by giving a manual input to the at least two sensor devices. As an alternative, the manual input is given to one sensor device which notifies the fact to at least one other sensor device. The at least two sensor devices are then in a synchronized state, which means that they know the relative position between them. The change of the relative position between the at least two sensor device can then be tracked, for example from the sensor data.

As another option, anatomical data from a previous diagnostic step or other examinations are used to increase the accuracy of the determined relative position and/or to limit the degrees of freedom when the relative position is determined. If, for example, the anatomical data preclude the determined relative position between the at least two sensor devices, then this may be indicated and/or the relative position can be determined again. If, for example, one sensor device is used as a marker device of a pointer, then implausible relative positions between two sensor devices can be precluded from the information about the point to be sampled.

The method in accordance with the invention is in particular a data processing method. The data processing method is preferably performed using technical means, in particular a computer. In particular, the data processing method is executed by or on the computer. The computer in particular comprises a processor and a memory in order to process the data, in particular electronically and/or optically. The calculating steps described are in particular performed by a computer. Determining or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term of computer encompasses a cloud computer, in particular a cloud server. The term of cloud computer encompasses cloud computer system in particular comprises a system of at least one cloud computer, in particular plural operatively interconnected cloud computers such as a server farm. Preferably, the cloud computer is connected to a wide area network such as the world wide web (WWW). Such a cloud computer is located in a so-called cloud of computers which are all connected to the world wide web. Such an infrastructure is used for cloud computing which describes computation, software, data access and storage services that do not require end-user knowledge of physical location and configuration of the computer that delivers a specific service. In particular, the term "cloud" is used as a metaphor for the internet (world wide web). In particular, the cloud provides computing infrastructure as a service (IaaS). The cloud computer may function as a virtual host for an operating system and/or data processing application which is used for executing the inventive method. Preferably, the cloud computer is an elastic compute cloud (EC2) provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals represent in particular the data received or outputted by the computer.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Within the framework of the invention, computer program elements can be embodied by hardware and/or software (this includes firmware, resident software, micro-code, etc.).

Within the framework of the invention, computer program elements can take the form of a computer program product which can be embodied by a computer-usable, in particular computer-readable data storage medium comprising computer-usable, in particular computer-readable program instructions, “code” or a “computer program” embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit—CPU) which executes the computer program elements and optionally a volatile memory (in particular, a random access memory—RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. Preferably, the data storage medium is a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

BRIEF DESCRIPTION OF THE DRAWINGS

The present invention shall be explained in more detail with reference to the accompanying drawings. The figures show.

DETAILED DESCRIPTION

Figures 1, 2:
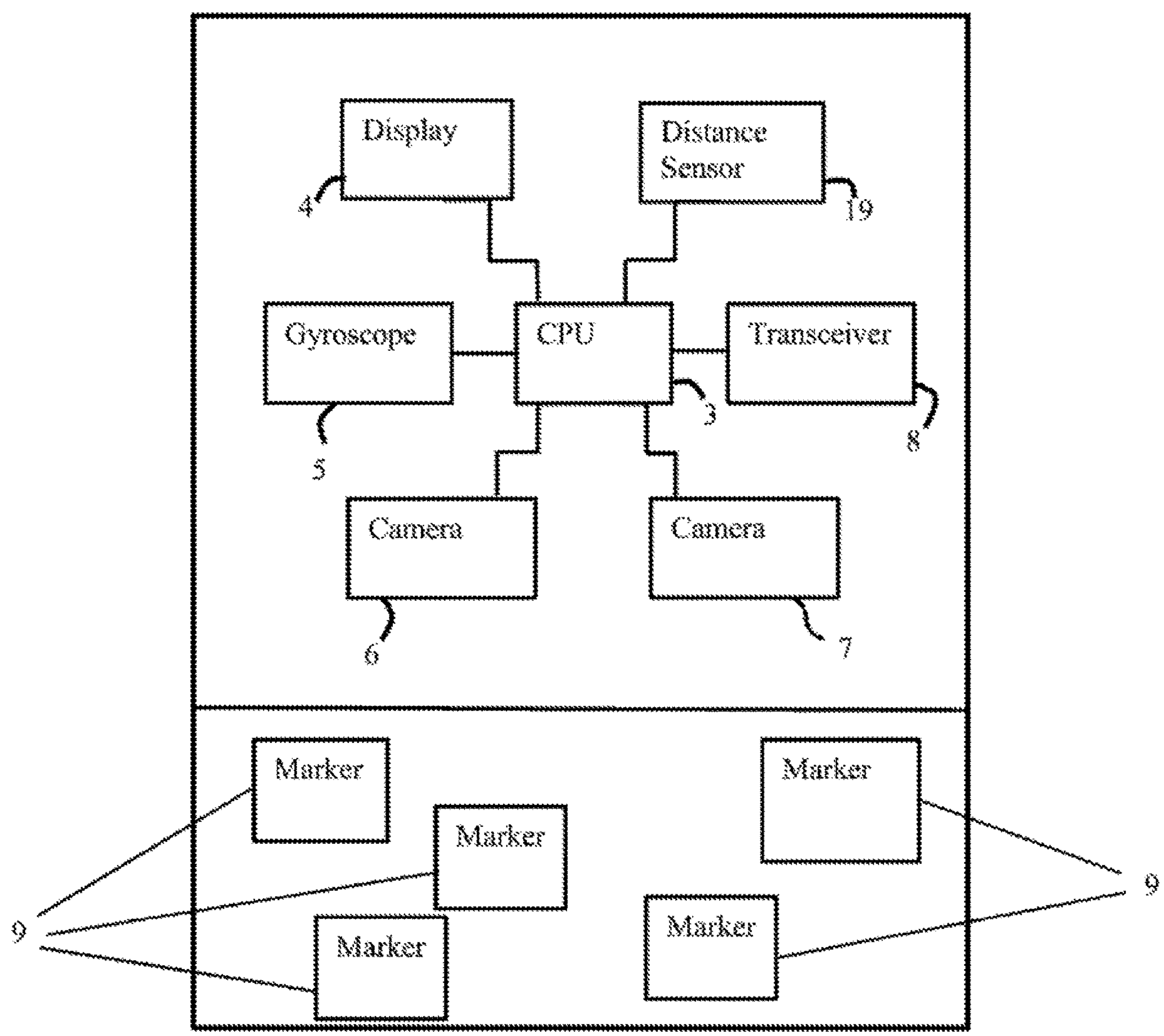
FIG. 1 a schematic structure of a medical tracking system.
FIG. 2 a schematic structure of a sensor device.

FIG. 1 schematically shows a medical tracking system, also referred to as a medical navigation system, comprising two sensor devices 1 and 2. The structure of the sensor devices 1 and 2 is shown schematically in FIG. 2.

In this exemplary example, a sensor device 1, 2 comprises a processor or central processing unit (CPU) 3 which is connected to a display 4, the gyroscope 5, two cameras 6 and 7 and a Bluetooth transceiver 8. The 2D-cameras 6 and 7 are located on opposite sides of a housing of the sensor device 1, 2. Preferably, camera 6 is located on the same side as the display 4. The cameras 6 and 7 act as position sensors. A sensor device 1,2 further comprises an optional distance sensor 19.

The gyroscope 5 is configured to determine orientation data which represent the orientation of the sensor device 1, 2 in three rotational dimensions in an absolute, ground-fixed reference system based on the direction of gravity. The gyroscope 5 acts as an orientation sensor. The processor 3 acts as control unit. This means that both sensor devices 1, 2 comprise a control unit.

At least one of the sensor devices 1, 2 comprises optical markers 9, which in the present case are rectangles or squares. The markers 9 have the same size and are arranged in a known pattern. This pattern is preferably three-dimensional, which means that the markers 9 are preferably arranged in two or more (parallel) planes. The sizes of some or all of the markers 9 can also be different. The shape of a sensor device can also be used as a marker.

FIGS. 3 to 12 show different steps of a first medical navigation workflow. In the exemplary application of the first workflow, the properties of a knee joint between a femur F and a tibia T are determined.

Figure 3:
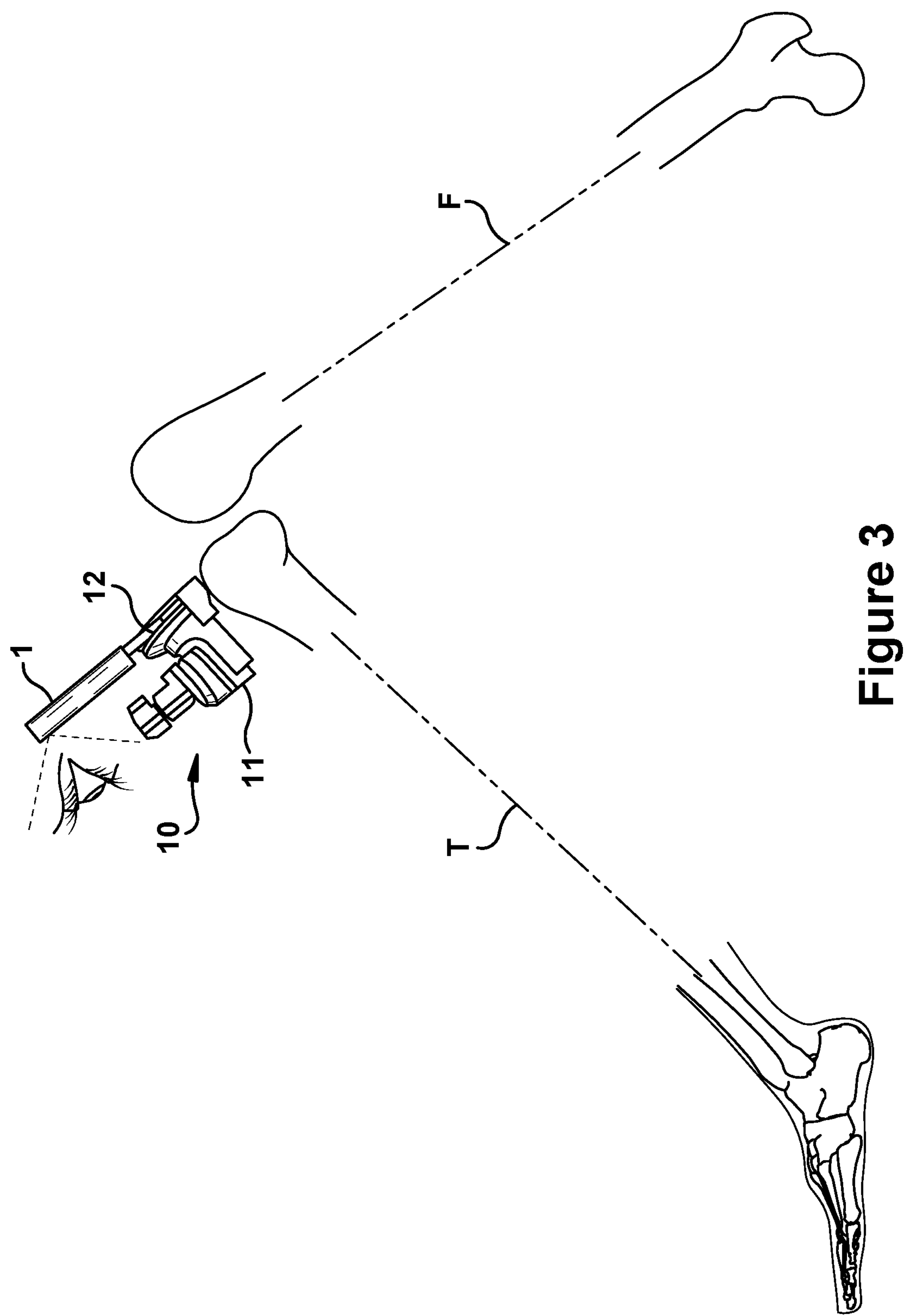
FIGS. 3 to 12 visualizations of steps of first medical navigation workflow, and FIGS. 13 to 16 visualizations of steps of a second medical navigation workflow.

In the step shown in FIG. 3, an adjustable cutting block 10 is attached to the tibia T. The adjustable cutting block 10 comprises a base 11 and an adjustable cutting slot 12 which is adjustable relative to the base 11. The first sensor device 1 is rigidly attached to the cutting slot 12 of the cutting block 10 in a reproducible position relative to the slot 12. The field of view of the camera 7 is indicated schematically by the eye symbol.

Figure 4:
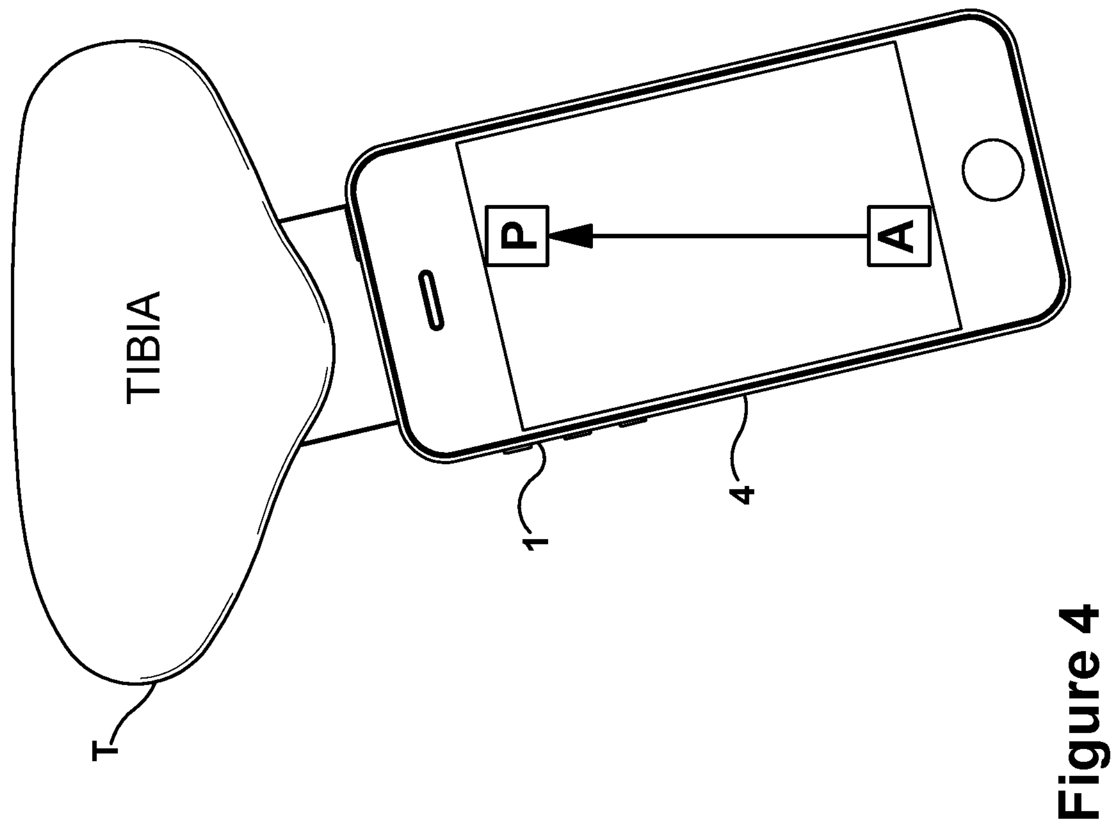
Figure 4:
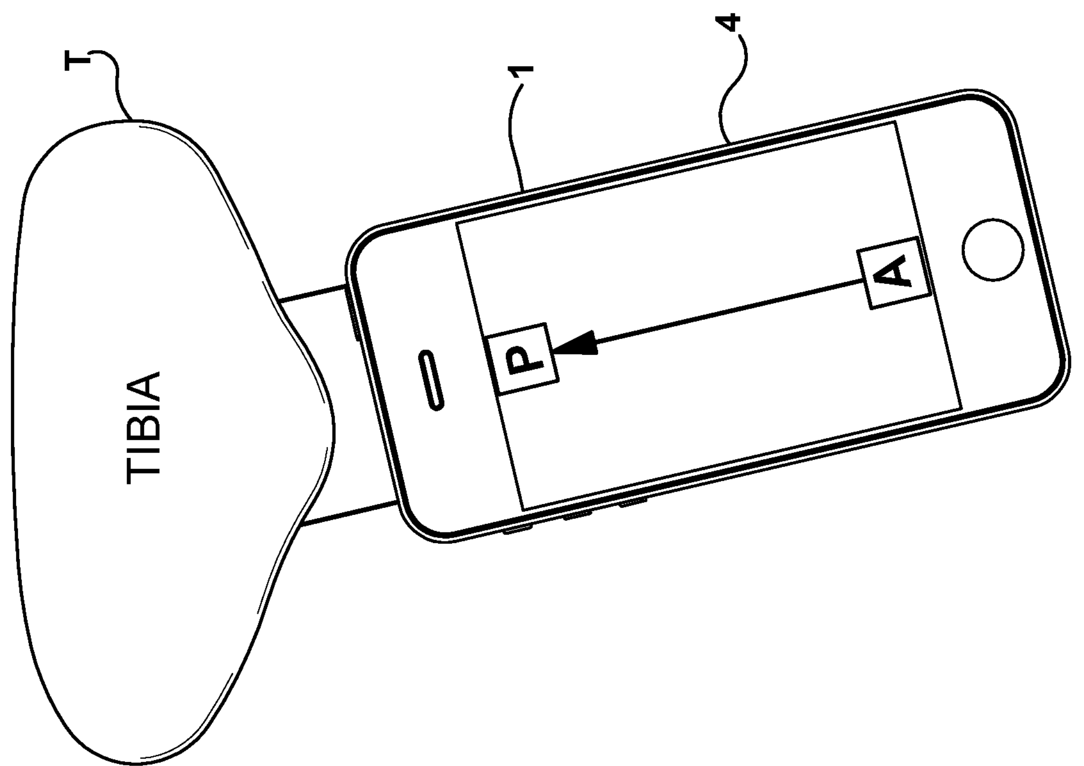

In the workflow step shown in FIG. 4, the sensor device 1 acquires the anterioposterior (AP) axis or direction as a property of the tibia T. The AP direction can be determined automatically, for example if the patient is lying flat on his back. In this case, the AP direction can be acquired as being parallel or in a known relation to gravity.

In the implementation shown in FIG. 4, the AP direction is acquired based on manually inputted AP data. In this case, an arrow virtually representing the AP direction is displayed on the display 4. A user can then input data to align the AP arrow shown on the display 4 with the actual AP direction of the tibia T. For this purpose, the AP arrow can be rotated in the display plane, for example by using buttons (not shown) of the sensor device 1 or by touching the display 4 if the display 4 is a touch sensitive display.

As a preferred option, the AP arrow is overlaid on an image captured by the camera 7 which is located in the housing of the sensor device 1 on an opposite side of the display 4. This image typically shows a part of the tibia, and preferably also a part of the foot. This overlay leads to an improved accuracy of the manually inputted AP direction. In addition or as an alternative, the AP direction can be automatically determined from an image analysis performed by the CPU 3.

In general, any property of an anatomical structure can be acquired by manipulating information, such as an arrow, displayed on the display of a sensor device.

In the workflow steps shown in FIGS. 5 and 6, the second sensor device 2, which comprises markers 9 as explained with reference to FIG. 2, is rigidly attached to a pointer 13. The relative position between the markers 9 and the tip of the pointer 13 is known. Additional markers, such as the circles 14, can be displayed on the display 4 of the sensor device 2. In this workflow step, the second sensor device 2 acts as a marker device and the first sensor device 1 acts as a marker device detector. In a modification of this example, there are no fixed markers 9, but only markers 14 displayed on the display 4.

The pointer 13 comprises an adaptor for accommodating a sensor device 1 or 2 in an unambiguous, reproducible position relative to its tip. Some or all of the fixed markers 9 may be located on the pointer 13.

In the medical workflow, landmarks of the tibia T are sampled by touching the landmark with the tip of the pointer 13 and determining the position of the markers 9 and 14. Due to the known constellation of the markers relative to the tip of the pointer 13, the position of the tip can be determined from the position of the markers. The positions of the markers are determined by the sensor device 1. The camera 7 of the sensor device 1 captures an image comprising the markers. Due to the known constellation and sizes of the markers, the CPU 3 of the sensor device 1 can analyze the output image of the camera 7 in order to detect the markers and hence the positions of the landmarks in a reference system of the sensor device 1. The CPU 3 uses the size, the shape and the relative positions of the markers in the output image of the camera to determine the position of the tip of the pointer. The position of the markers may be more accurate by using the distance sensor 19, such as a laser beam generator, to calculate the distance of the markers from the sensor device.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (in particular on the surface of) a characteristic anatomical structure of the body part can also represent said structure. The landmark can represent the anatomical structure as a whole or only a point or part of it. A landmark can also for example lie on the anatomical structure, which is in particular a prominent structure. An example of such an anatomical structure is the posterior aspect of the iliac crest. Other landmarks include a landmark defined by the rim of the acetabulum, for instance by the centre of the rim. In another example, a landmark represents the bottom or deepest point of an acetabulum, which is derived from a multitude of detection points. Thus, one landmark can in particular represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational centre of the femur head when moved relative to the acetabulum.

A detection point is in particular a point on the surface of the anatomical structure which is detected, for example by a pointer.

Figure 5:
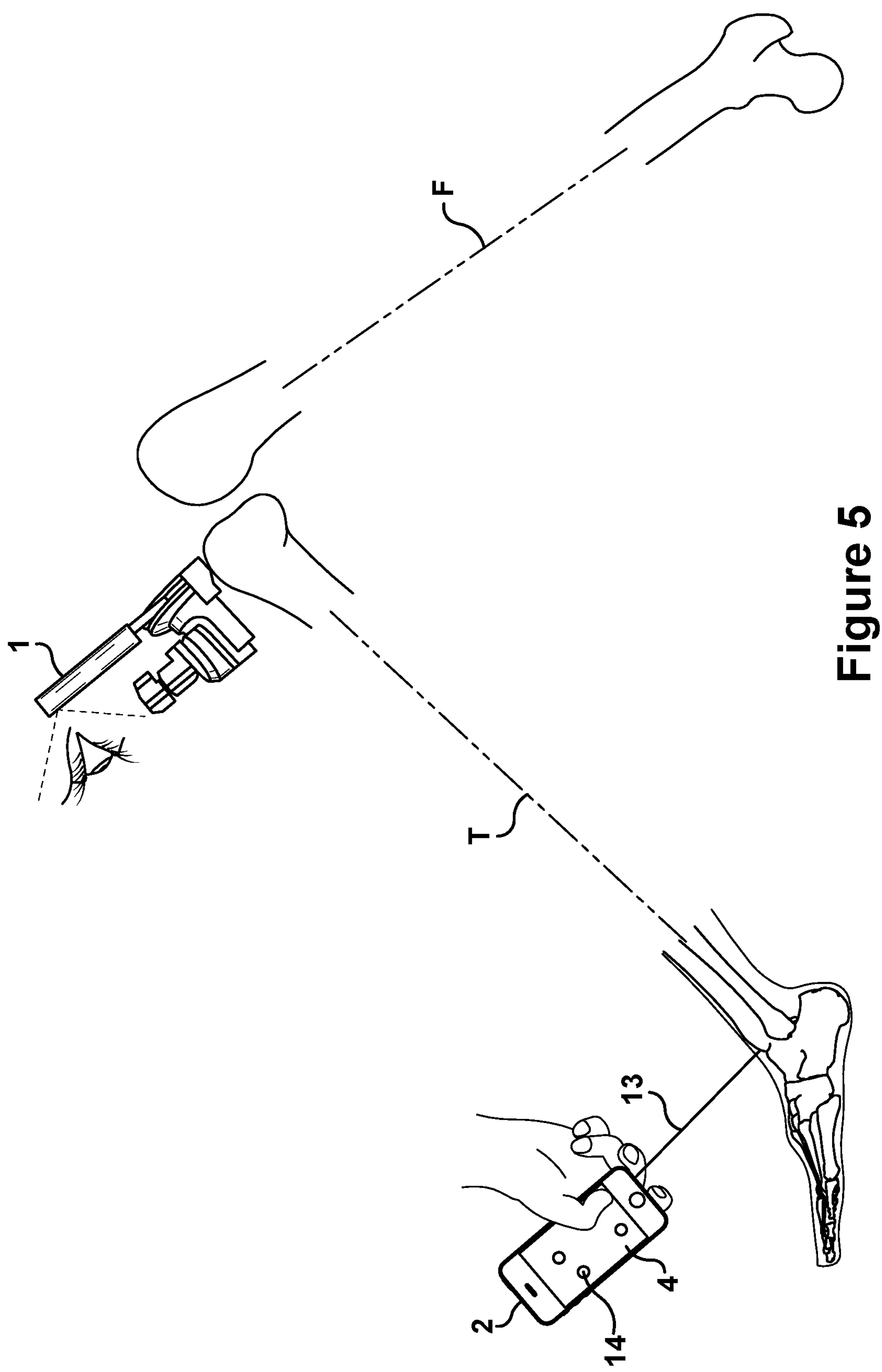

In the workflow step shown in FIG. 5, the lateral and medial malleolus landmarks are determined. In the workflow step shown in FIG. 6, the proximal endpoint of the tibia mechanical axis is sampled. With the sampled landmarks and the acquired AP direction, the tibia T is now registered relative to the sensor device 1. For the workflow step shown in FIG. 6, the sensor device 1 switches to the other camera 6, which captures a volume different from the volume captured by camera 7.

With the tibia T being registered, the mechanical axis of the tibia T is known. The reference system of the sensor device 1 is in a known relation to the cutting slot 12. As long as the adjustment of the cutting slot 12 is not changed compared to the base 11, then the registration is also known with the base 11 as a reference.

In the next workflow steps, the femur F is registered. In the workflow step shown in FIG. 7, the sensor device 2 is rigidly attached to an adjustable cutting block 15. A cutting block 15 comprises a base 16 which is rigidly attached to the femur F and a cutting slot 17 which is adjustable relative to the base 16. The sensor device 1 is attached to the cutting slot 17.

Figure 8:
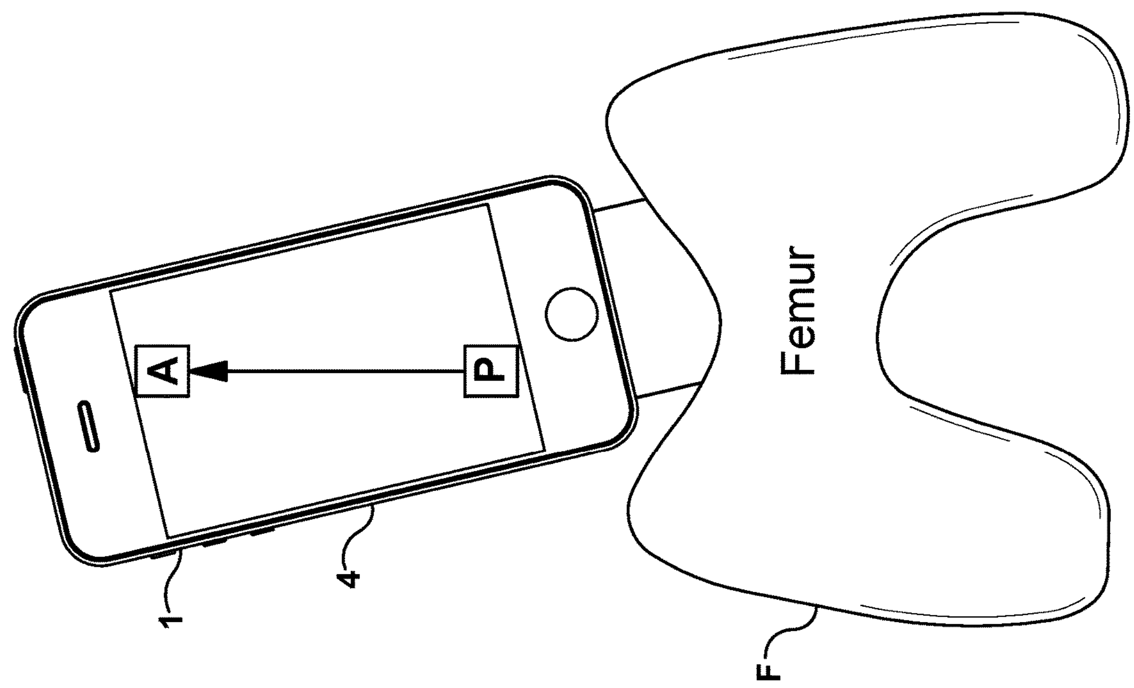
Figure 8:
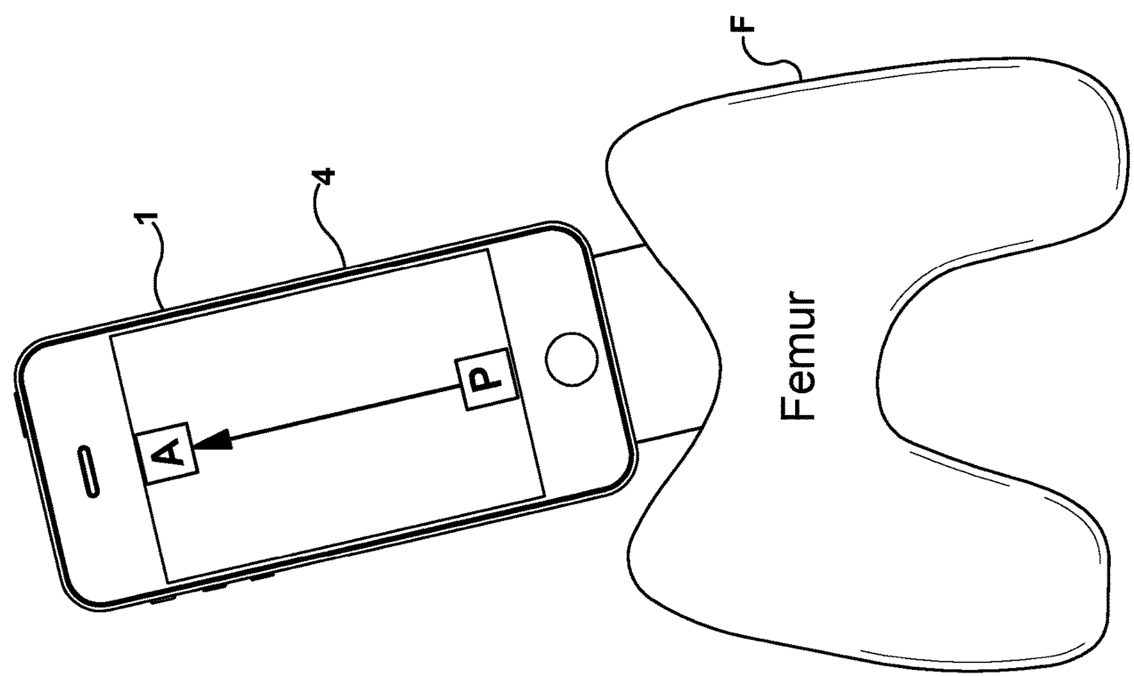

In the workflow step shown in FIG. 8, the AP direction of the femur is acquired. The possibilities for acquiring the AP direction of the femur F are analog to the possibilities described for the tibia with reference to FIG. 4, such that a detailed explanation is omitted.

Figure 9:
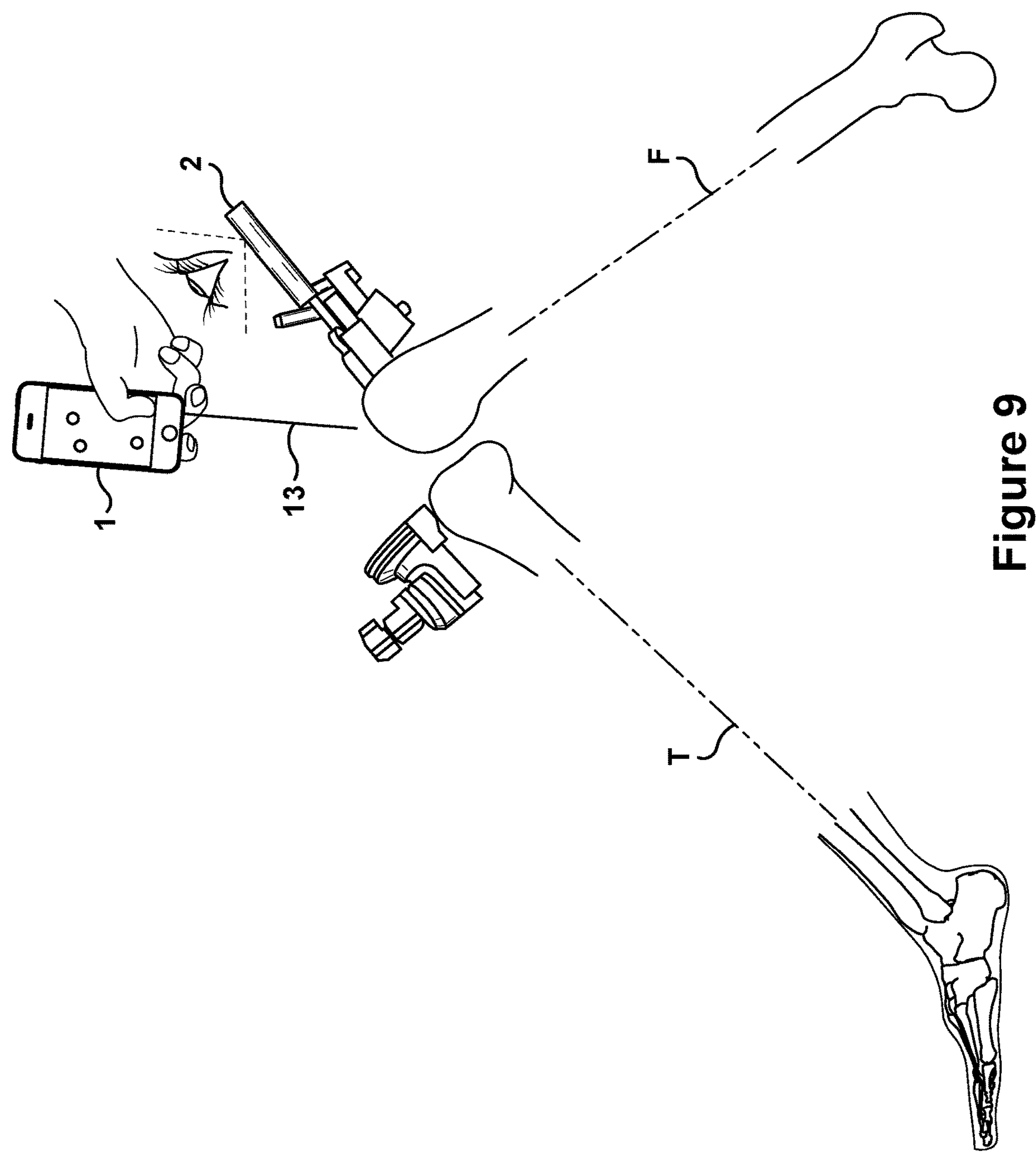

In the workflow step shown in FIG. 9, the sensor device 1 is used in combination with the pointer 13 to sample the distal end point of the femoral axis.

Figure 10:
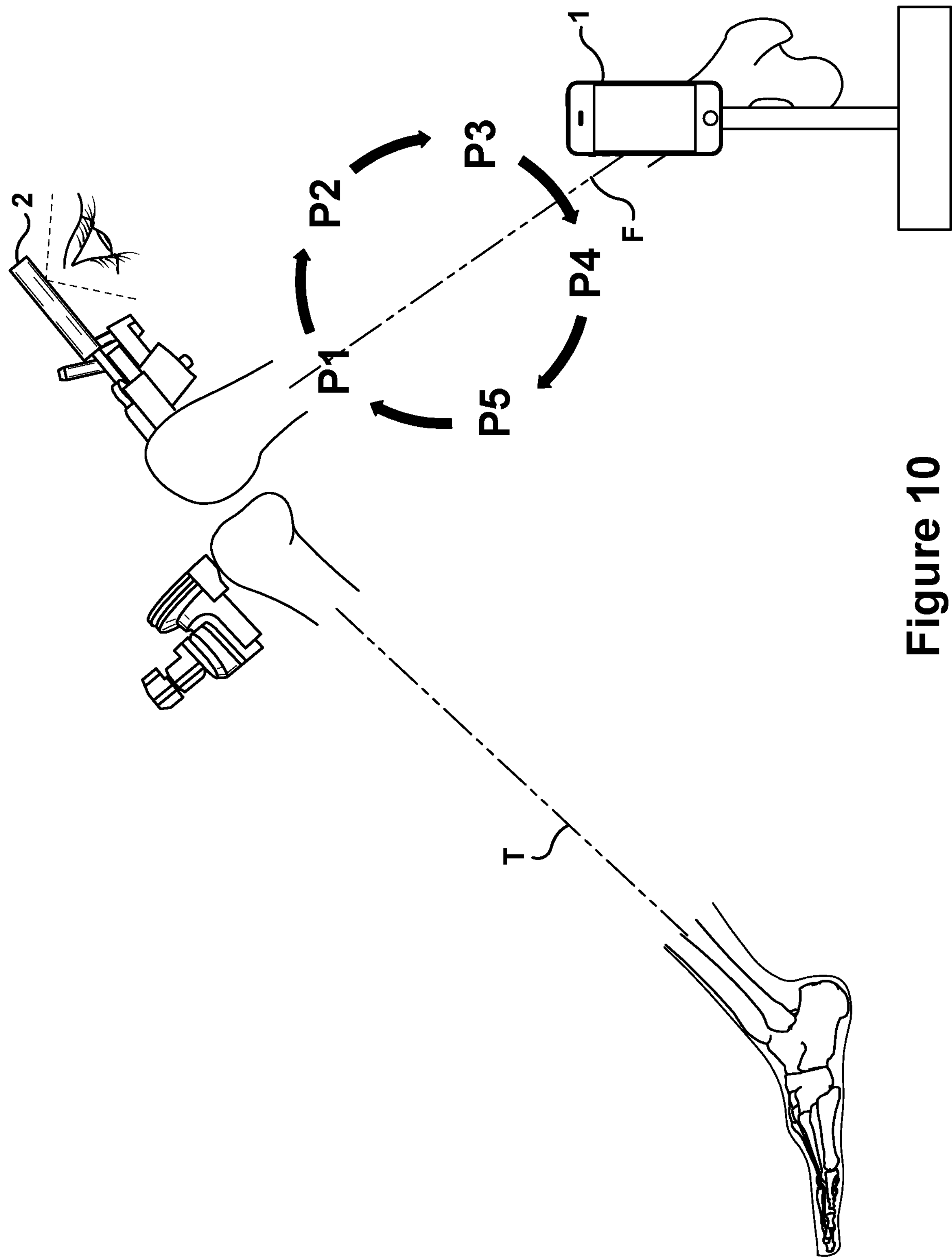

In the workflow step shown in FIG. 10, the sensor device 1 is detached from the pointer 13 and rigidly fixed in an absolute position. For example, the sensor device 1 is rigidly attached to a tripod or an operation room table, in particular to a rail of the table. Then, the femur F is pivoted about its head. This means that the sensor device 2 moves on a spherical shell centered about the center of the femoral head. Using a camera 6 or 7, the CPU 3 of the sensor device 2 determines the relative position of the sensor device 2 by detecting the markers 9 and 14 of the sensor device 1 in analogy to the step described with reference to FIGS. 5, 6 and 9. From the plurality of relative positions P1 to P5 of the sensor device 2 relative to the sensor device 1 and the known fact that the sensor device 2 moves on spherical shell about a fixed center, this center, which is the center of the femoral head, can be calculated.

Now that the distal endpoint of the femoral axis, the center of the femoral head and the AP direction of the femur F are known, the femur F is registered in a reference system of the sensor device 2, which is in a fixed relation to a reference system of the cutting slot 17.

In the workflow steps shown in FIGS. 9 and 10, the first sensor device 1 acts as a marker device and the second sensor device 2 acts as a marker device detector. In general, the function of a sensor device 1 or 2, that is whether a sensor device acts as a marker device or a marker detector device, is selected by a CPU 3 based on the currently performed workflow step.

For the workflow step shown in FIG. 11, the first sensor device 1 is re-attached to the cutting slot 12 of the cutting block 10 in the same relative position to the cutting slot 12 as in the workflow steps explained with reference to FIGS. 3 to 6. This means that, as long as the cutting blocks 10 and 15 are not adjusted, the sensor device 1 is in a fixed relative and registered position to the tibia T and the sensor device 2 is in a fixed relative and registered position to the femur F.

Figure 11:
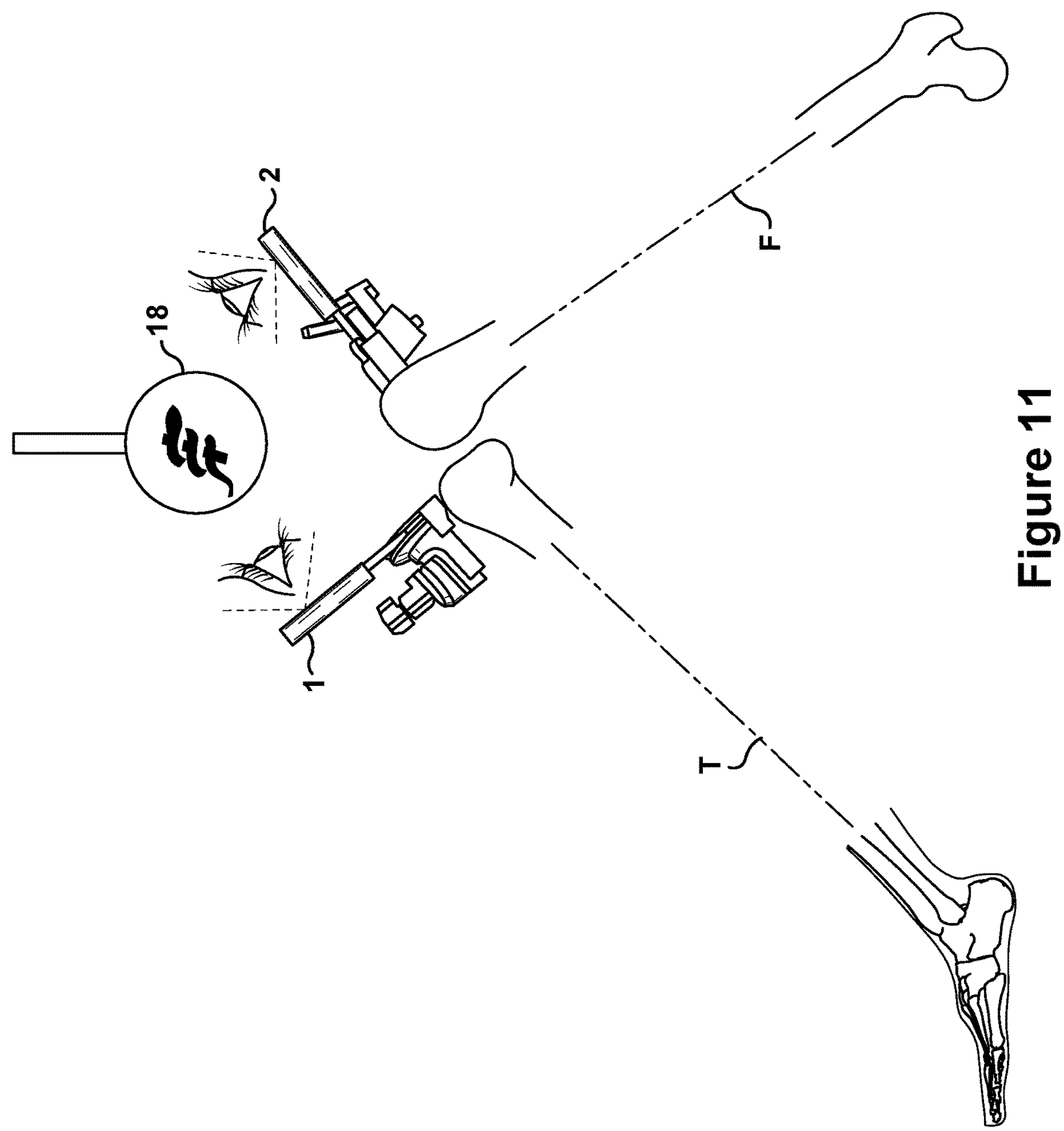

In the workflow step shown in FIG. 11, a measurement of the relative position between the two sensor devices 1 and 2 is performed, including the step of exchanging sensor data and using a reference. Exchanging means that at least one of the sensor devices transmits its sensor data, like the orientation data acquired by its gyroscope 5, to the other sensor device using the Bluetooth transceivers 8. Preferably, both sensor devices 1 and 2 exchange their respective orientation data, such that the CPUs 3 of both sensor devices 1 and 2 know the sensor data, like the orientation data, of both sensor devices. In this implementation, the gravity field of the earth acts as a reference for the synchronization.

In addition or as an alternative, a reference object 18 is used as a reference. In this implementation, the reference object 18 is imaged by at least one camera 6 or 7 of each sensor device 1 and 2. By image analysis, the relative position of the reference object 18 relative to the sensor devices 1 and 2 is calculated by the respective CPU 3. The position data representing the relative position of the reference object 18 to a sensor device is then transmitted to the other sensor device using the Bluetooth transceivers 7. In this implementation, again, the position information of (just) one sensor device can be transmitted to the other sensor device, or each sensor device can receive the position data from the other sensor device.

After measurement of the relative position, at least one of the sensor devices 1 or 2 knows the relative position, this means at least the relative orientation in three-rotational dimensions, of the other sensor device in its own reference system. The relative spatial location is not needed in the present workflow, but may also be determined. Since the tibia T and the femur F are registered, the sensor device thus also knows the relative position of the femur F and the tibia T. Preferably, the registration data representing the relation of the bone and the sensor device is also transmitted to the other sensor device. This, again, is performed either in one direction only or both sensor devices transmit the registration data.

Figure 6:
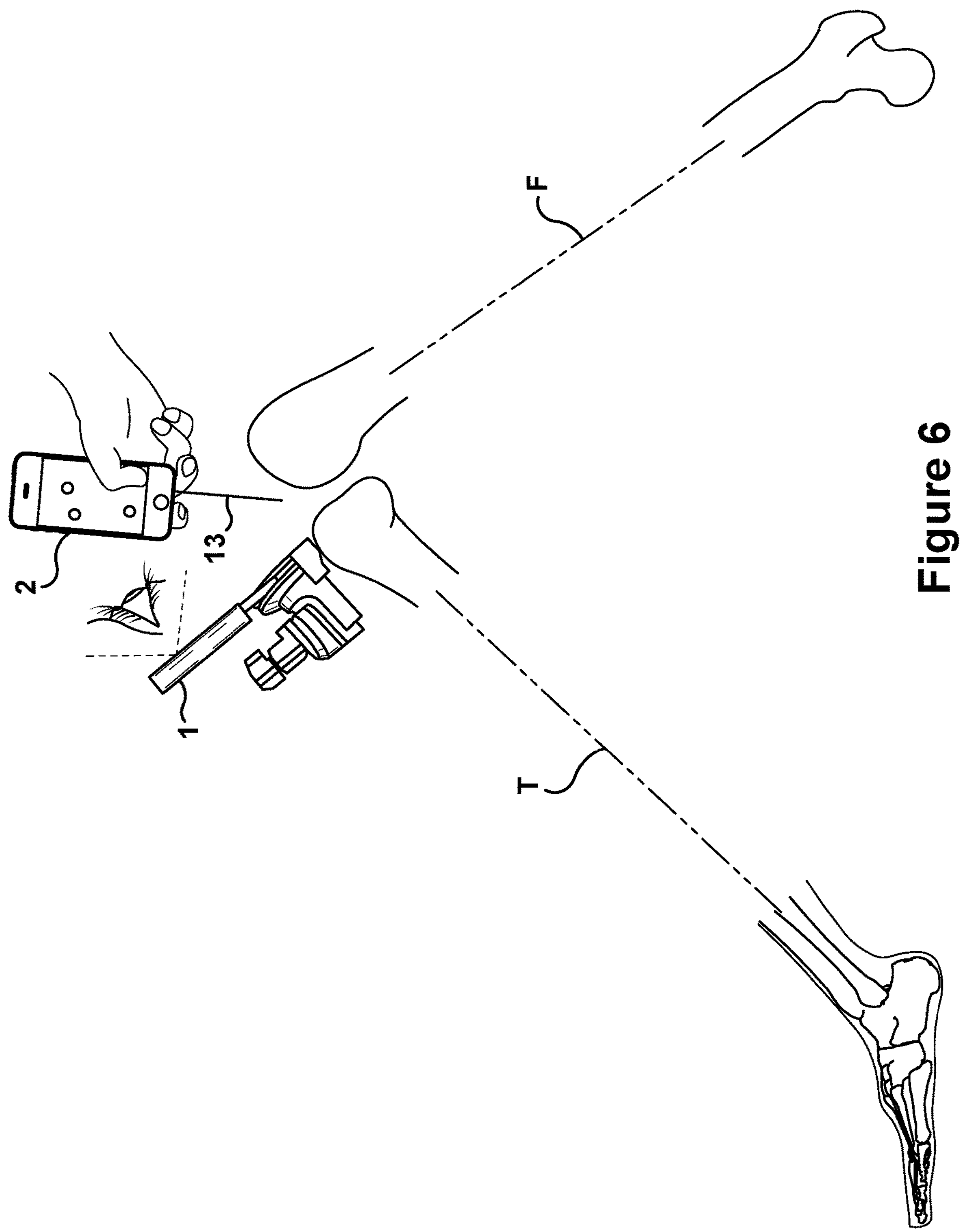
Figure 7:
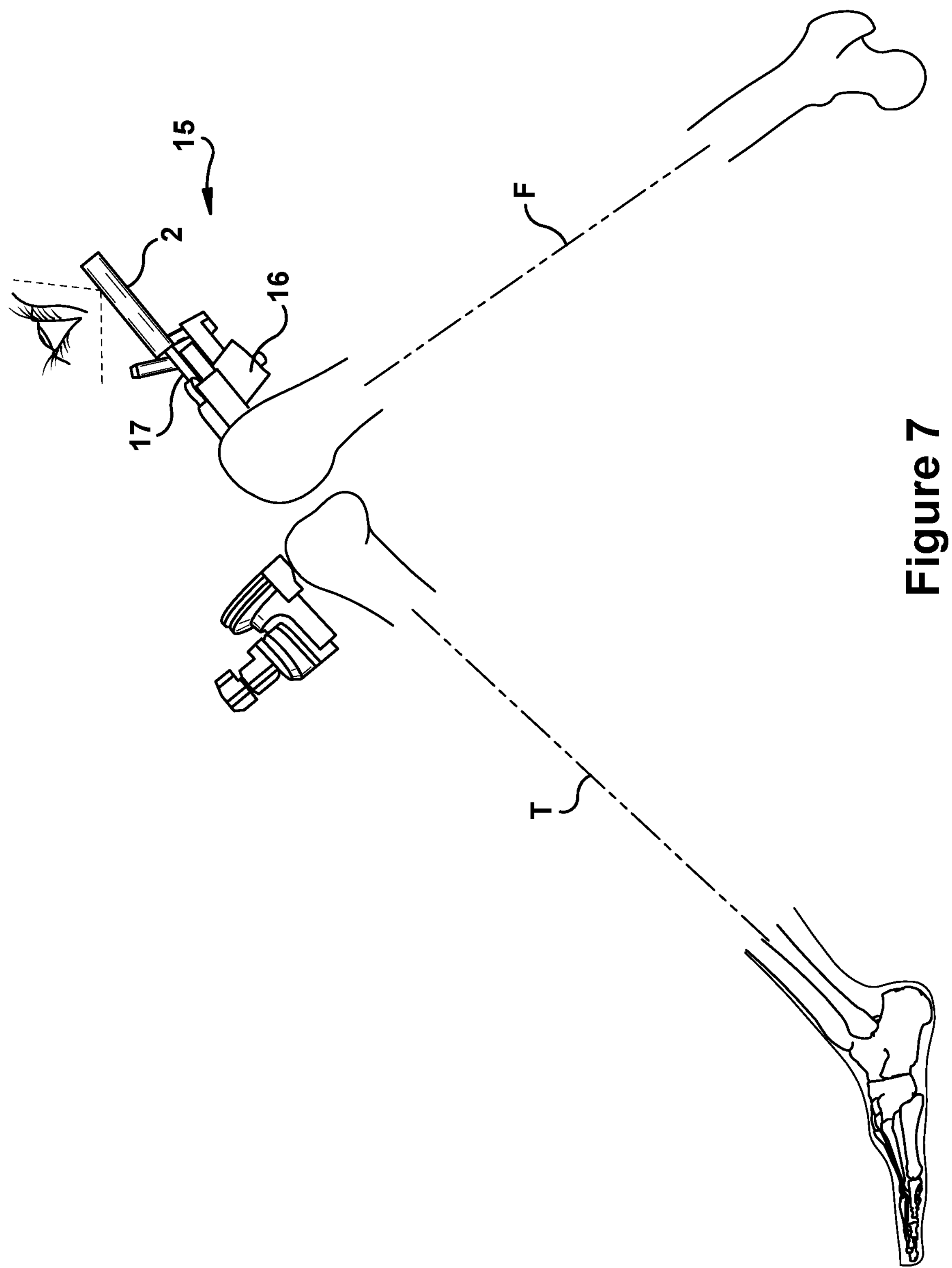

This approach for determining the relative position between the two sensor devices can also be used if one of the sensor devices is used as a marker device detector, such as in the workflow step shown in FIGS. 5 and 6, either replacing or supplementing the use of the markers.

Figure 12:
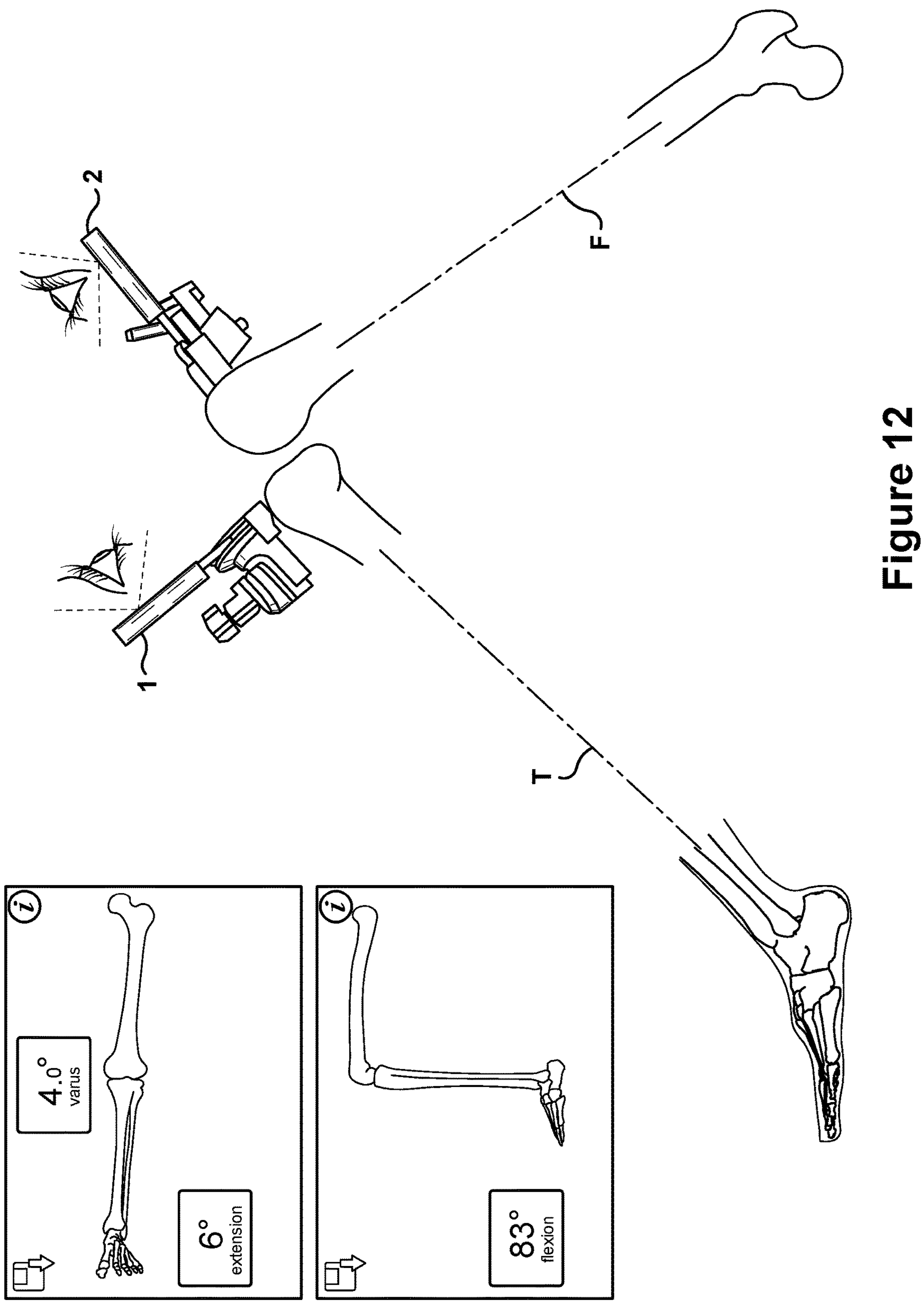

In the workflow step shown in FIG. 12, the tibia T is moved relative to the femur F using the knee joint. A measurement of the relative positions between the sensor devices 1 and 2 is performed in a plurality of positions. For each measurement, the sensor devices 1 and 2 exchange their orientation data and/or the position data of the reference object 18 such that at least one of the CPUs 3 can calculate the relative position of the sensor devices 1 and 2, and therefore of the femur F and the tibia T. If one measurement is taken in fill extension and one measurement is taken in full flexion of the joint, then the range of motion of the knee joint can be determined. From the relative position, also the varus or valgus angle can be determined. The values of the range of motion as well as the varus/valgus value may be shown on the display 4 of a sensor device, such as depicted in the screenshots in the upper left of FIG. 12.

FIGS. 13 to 16 show steps of a second medical workflow. These steps require the registration of the tibia T and the femur F as explained above with reference to FIGS. 4 to 6 and 8 to 10, with the same preconditions that an adjustable cutting block 10 is attached to the tibia T and an adjustable cutting block 15 is attached to the femur F. The positional relation between the sensor device 1 and the cutting slot 12 is known, as is the positional relation between the sensor device 2 and the cutting slot 17.

Figure 13:
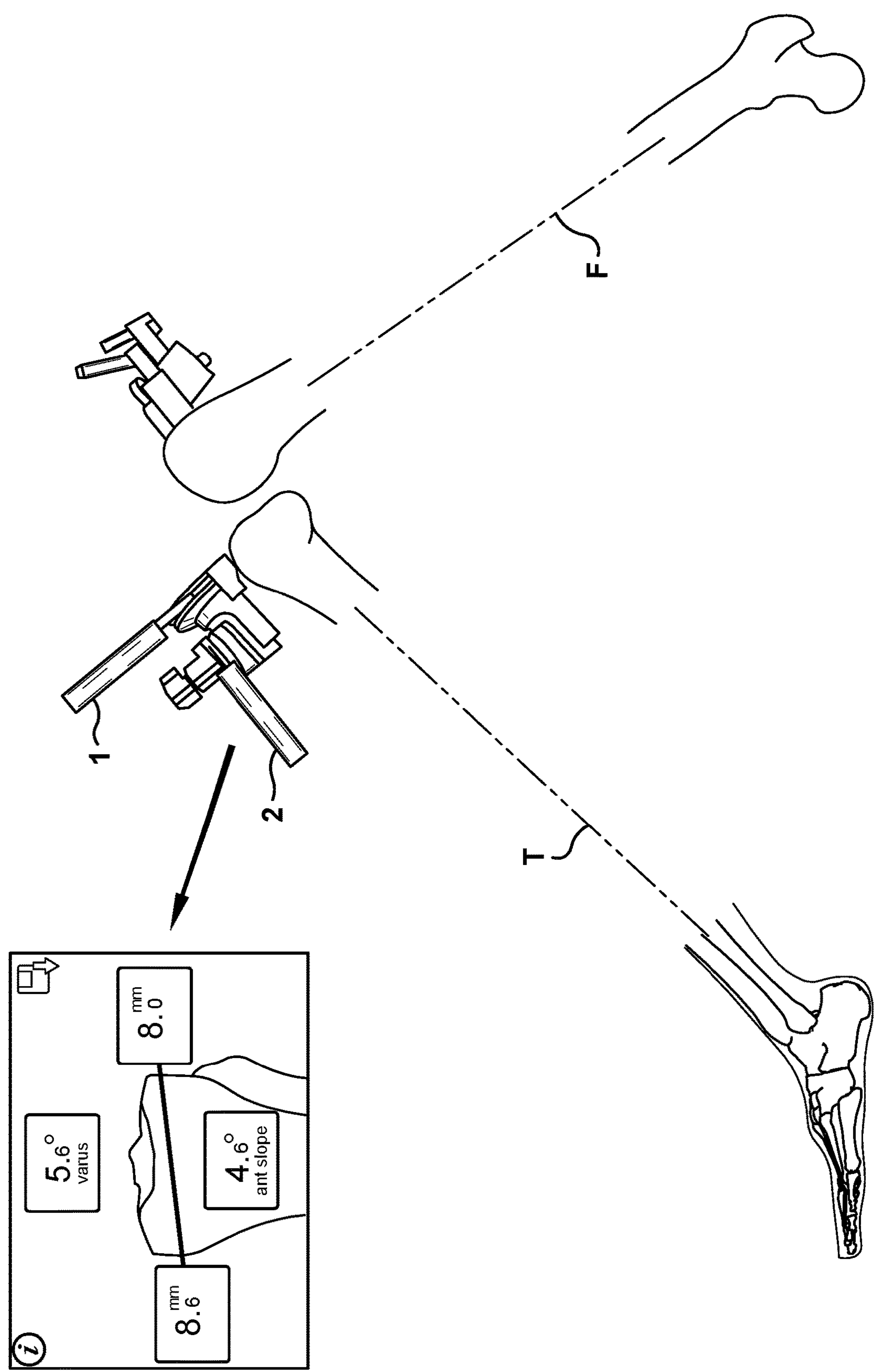

In the workflow step shown in FIG. 13, the sensor device 1 is rigidly attached to the cutting slot 12 and the sensor device 2 is rigidly attached to the base 11 of the cutting block 10. With the registration of the tibia T in the reference system of the sensor device 1, and the known relation between the sensor device 1 and the cutting slot 12, the current adjustment of the cutting slot 12 relative to the tibia T can be shown on the display 4 of any of the sensor devices as indicated in the screenshot shown in the upper left of FIG. 13.

A first measurement of the relative position between the sensor devices 1 and 2 is then performed as explained above with reference to FIG. 11, If the cutting block 10 is then adjusted, the relative position between the sensor devices 1 and 2 changes. By repeatedly measuring the relative position and calculating the current slot adjustment relative to the tibia T from the relative position, the cutting slot 12 can be adjusted to a desired setting. For example, one of the sensor devices 1 and 2 can output indication information if the current adjustment of the cutting slot 12 relative to the tibia T equals the desired setting. This indication information can be of optical, acoustical or tactile nature.

In this workflow step, the adjustment of the cutting block 10 is tracked using the sensor device 2 as a reference. If the sensor device 1 would use gravity as a reference, then any movement of the tibia T would impair the adjustment of the cutting slot 12. This is overcome by using the sensor device 2, which is rigidly attached to the tibia T via the base 11 of the cutting block 10, as a reference and performing measurements of the relative position by exchanging the orientation data and/or position data.

Figure 14:
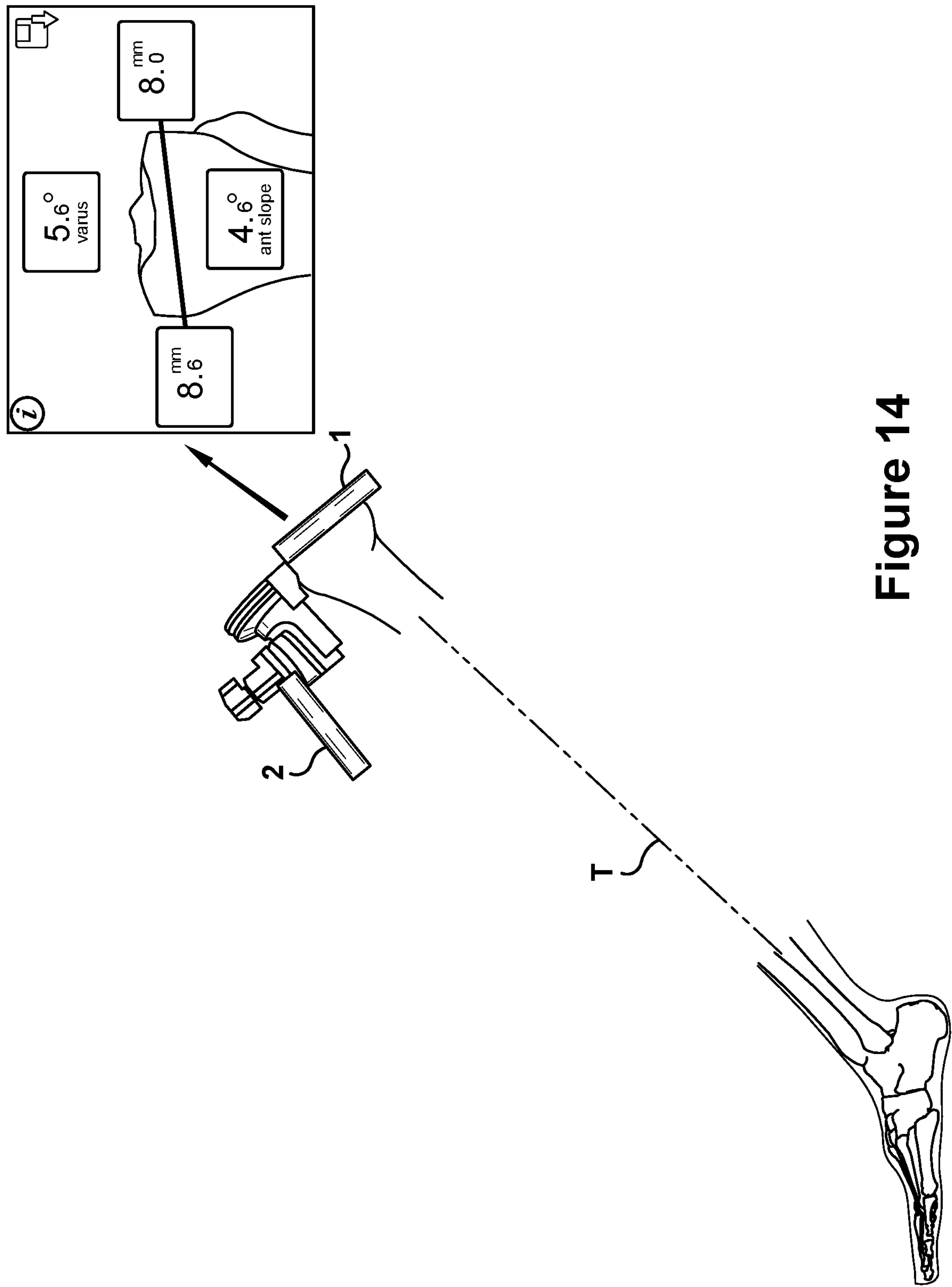

In the optional workflow step shown in FIG. 14, it is assumed that the cutting process of the tibia T has been performed. In this workflow step, a defined surface of the sensor device 1 is laid onto the cut surface of the tibia T. Then, a measurement of the relative position between the sensor devices 1 and 2 is performed. From this relative position, the position of the cut surface relative to the tibia T can be calculated for a verification step. As indicated in the screenshot in the upper right in FIG. 14, the actual position of the performed cut is displayed. By activating the disc symbol in the upper right of the screenshot, the actual position of the cut surface can be saved for documentation purposes.

Figure 15:
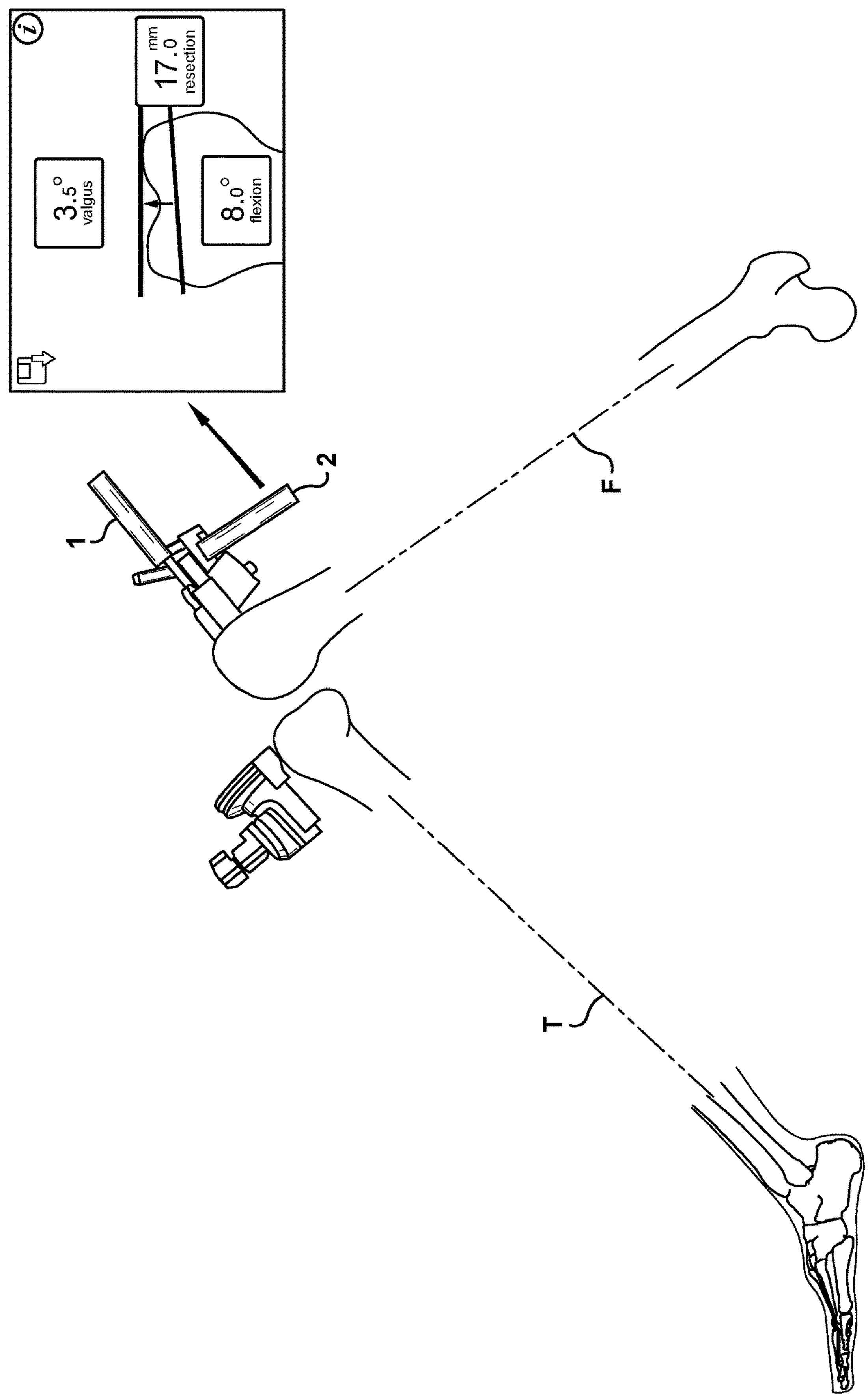

In the workflow step shown in FIG. 15, the cutting block 15 attached to the femur F is adjusted in analogy to the adjustment process of the cutting block 10 attached to the tibia T as described with reference to FIG. 13. However, for the adjustment of the cutting block 15, the sensor device 1 is rigidly attached to the base 16 and the sensor device 2 is rigidly attached to the cutting slot 17 of the cutting block 15.

Figure 16:
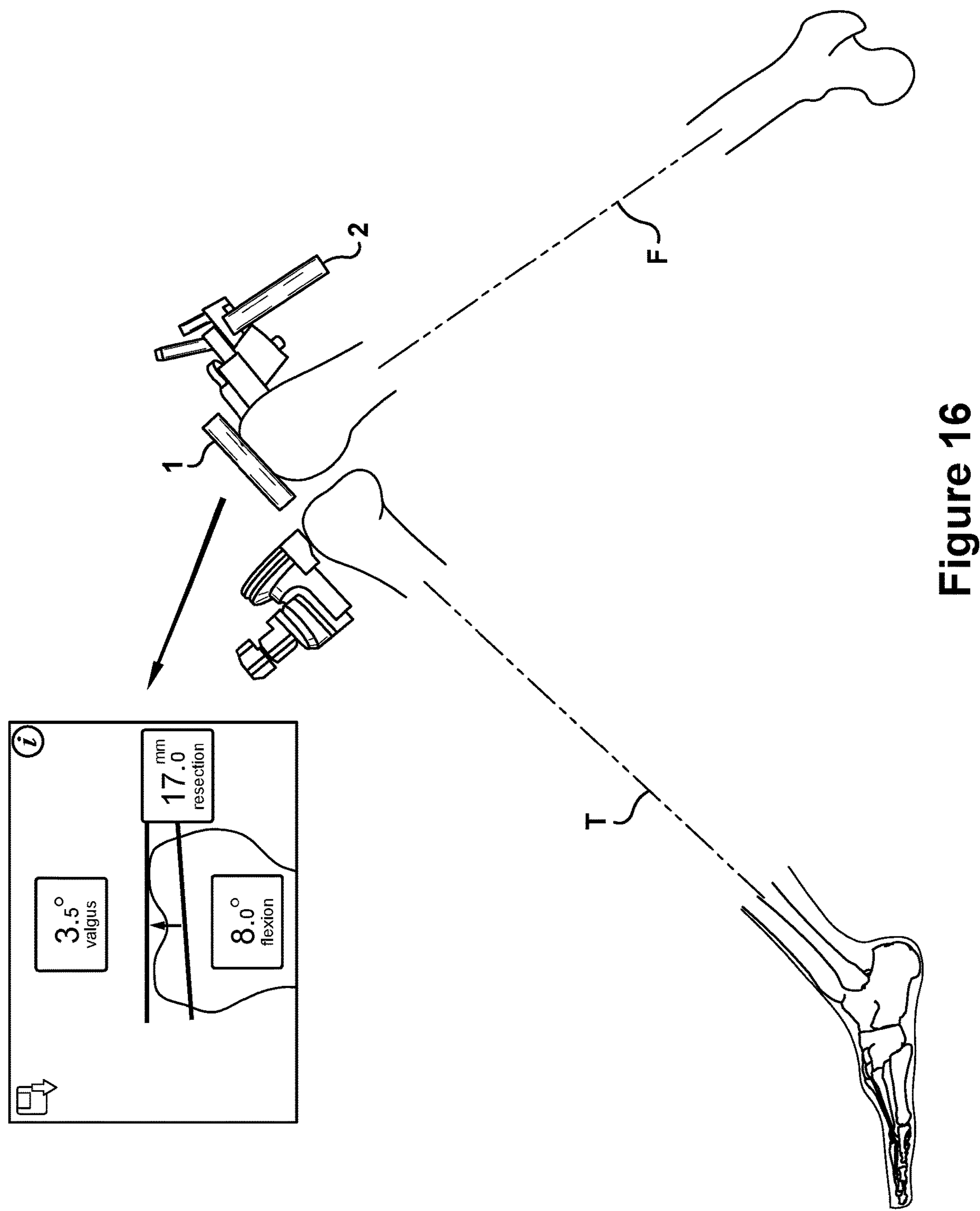

In the optional workflow step shown in FIG. 16, a defined surface of the sensor device 1 is laid onto the cut surface of the femur F. By measuring the relative position between the sensor devices 1 and 2, the cutting surface can be verified in analogy to the process described with reference to FIG. 14. Again, the actual position of the cut surface can be saved for documentation purposes by clicking on the disc symbol of the screenshot shown in the upper left of FIG. 16.

The desired setting of the cutting slot 12 or 17, respectively, can be calculated automatically based on a 3D image dataset representing a 3D image of the tibia or femur, respectively. In addition or as an alternative, the varus/valgus value and/or the range of motion acquired in the workflow step described with reference to FIG. 12 can be used for determining the desired setting.

When performing a medical workflow using the medical tracking system of this exemplary embodiment, the next step of the workflow is begun once the completion of the previous step is automatically detected or manually inputted. So the completion is typically known only to the sensor device which determines the completion. Thus, this sensor device preferably notifies to the other sensor device(s) of the tracking system that the next step is to be performed. This may result in one or more of the sensor devices to change its function from being a marker device to being a marker detection device or vice versa. In addition, a sensor device may display on its display 4 some guidance information on what to do in the next workflow step, thus leading the operator of the tracking system through the workflow.

A sensor device 1, 2 may further comprise an acceleration sensor (not shown). When the sensor data of the acceleration sensor is integrated over a period of time, this results in an information on the change of the position of the sensor device in this period of time. This information may also be exchanged between the sensor devices and used for calculating the relative position between the sensor devices.

It is to be noted that the methods and workflows described herein do not relate to or comprise any surgical step. In particular, attaching a cutting block to a bone and performing a cut are not part of the present invention. This invention solely relates to the step of navigating, tracking and verifying by acquiring and analyzing data.

Any embodiment described so far may be combined with one or more features of the following additional embodiments:

Embodiment 1

A medical tracking system comprising at least one sensor device (1, 2) which can be positioned in a fixed position relative to a target (10, 13, 15), the sensor device (1, 2) comprising a marker device (9, 14) and a marker device detector (6, 7), the marker device detector (6, 7) being capable of obtaining information for determining the position of a marker device (9, 14), the system further comprising a control unit (3) configured to process a medical navigation workflow and to select the function of the sensor device (1, 2) as either acting as a marker device detector or as a marker device in a step of the medical navigation workflow.

Embodiment 2

The tracking system of embodiment 1, wherein the sensor device (1, 2) comprises a display (4) for displaying at least a part (14) of the marker device.

Embodiment 3

The tracking system of embodiment 1 or 2, wherein the marker device (9, 14) is an optical marker device and the marker device detector (6, 7) is a still or video camera.

Embodiment 4

The tracking system of embodiment 3, wherein the optical marker device (9, 14) comprises a plurality of squares (9) in a known configuration.

Embodiment 5

The tracking system of any one of embodiments 1 to 4, wherein the tracking system comprises at least two sensor devices (1, 2), wherein, in a particular step of the medical navigation workflow, one sensor device (1, 2) acts as a marker device (9, 14) and another sensor device (1, 2) acts as a marker device detector (6, 7).

Embodiment 6

The tracking system of embodiment 5, wherein one of the sensor devices (1, 2) is positioned in a fixed position relative to a target (10, 15, F, T) and another sensor device acts as a pointer (13).

Embodiment 7

The tracking system of embodiment 5 or 6, wherein the sensor device acting as a marker device transmits the output data of its marker device detector, an orientation sensor (5) or an acceleration sensor as sensor data to the control unit (3), the sensor device (1, 2) acting as a marker detection device transmits the output data of its marker detection device (6, 7) as sensor data to the control unit (3) and the control unit (3) is configured to receive and combine the sensor data of the sensor devices (1, 2) in order to determine a relative position between two sensor devices (1, 2).

Embodiment 8

The tracking system according to any one of embodiments 1 to 7, wherein a sensor device (1, 2) further comprises an orientation sensor (5).

Embodiment 9

A method of medical tracking supporting a medical navigation workflow, comprising the steps of using a sensor device (1, 2) comprising a marker device (9, 14) and a marker device detector (6, 7) as a marker device detector in one step of the medical navigation workflow for obtaining information for determining the position of a marker device (9, 14) and using the same sensor device (1, 2) as a marker device in another step of the medical navigation workflow.

Embodiment 10

Thee method according to embodiment 9, wherein at least two sensor devices (1, 2) are used, one of the sensor devices (1, 2) acting as a marker device of a pointer (13) for pointing at sample points and another one of the sensor devices (1, 2), being positioned in a fixed position relative to a target (10, 15, F, T), acting as a marker device detector for obtaining information for determining the position of the marker device (9, 14).

Embodiment 11

The method according to embodiment 10, further comprising the step of registering the target (10, 15, F, T) by sampling a plurality of sample points.

Embodiment 12

The method of embodiment 10 or 11, wherein the sensor device (1, 2) acting as a marker device and the sensor device (1, 2) acting as a marker device detector both comprise an orientation sensor (5) and the orientation sensor data are used when the position of a marker device is determined.

Embodiment 13

The method of any one of embodiments 9 to 12, further comprising the steps of determining sensor data comprising at least one of orientation data, position data and acceleration data with two or more of the sensor devices (1, 2)

transferring the sensor data to a control unit (3) and determining the relative position between two sensor devices (1, 2) by the control unit (3) by combining the sensor data.

Embodiment 14

The method of any one of embodiment 9 to 13, wherein the marker detector (6, 7) is a camera and the sensor device (1, 2) farther comprises a display device (4) and is positioned in a fixed position relative to a bone (F, T), wherein the image captured by the camera (6, 7) is displayed on the display device (4) and a characteristic property of the bone (F, T) can be input based on the camera image on the display device (4).

What is claimed:

1. A medical tracking system for determining a relative position between first and second associated targets, the medical tracking system comprising:

a reference object disposed at a fixed position;

a first independently maneuverable sensor device comprising:

a first housing configured to be rigidly attached with the first associated target;

a first memory device in the first housing, the first memory device storing first registration data representative of a relationship between the first sensor device and the first associated target when the first sensor device is rigidly attached with the first associated target;

a first processing unit in the first housing and operatively coupled with the first memory device; and a first camera in the first housing and operatively coupled with the first processing unit, wherein the first camera is operable to generate first image data representative of a first image of the reference object captured by the first camera, wherein the first processing unit is operable to calculate based on the first image data a first relative position comprising a first calculated position of the reference object relative to the first sensor device comprising:

a first spatial location in three translational dimensions between the reference object and the first sensor device; and/or a first alignment in three rotational dimensions between the reference object and the first sensor device;

a second independently maneuverable sensor device comprising:

a second housing different than the first housing, the second housing being configured to be rigidly attached with the second associated target;

a second memory device in the second housing, the second memory device storing second registration data representative of a relationship between the second sensor device and the second associated target when the second sensor device is rigidly attached with the second associated target;

a second processing unit in the second housing and operatively coupled with the second memory device; and a second camera in the second housing and operatively coupled with the second processing unit, wherein the second camera is operable to generate second image data representative of a second image of the reference object captured by the second camera, wherein the second processing unit is operable to calculate based on the second image data a second relative position comprising a second calculated position of the reference object relative to the second sensor device comprising:

a second spatial location in three translational dimensions between the reference object and the second sensor device; and/or a second alignment in three rotational dimensions between the reference object and the second sensor device; and a control unit operable to calculate based on: i) the first relative position comprising the first calculated position of the reference object relative to the first sensor device; ii) the second relative position comprising the second calculated position of the reference object relative to the second sensor device; and iii) one or more of the first registration data and/or the second registration data, at least one of:

a third relative position comprising a third calculated position of the first associated target relative to the second associated target; and/or a fourth relative position comprising a fourth calculated position of the second associated target relative to the first associated target.

2. The medical tracking system according to claim 1, further comprising:

a first distance sensor in the first housing operable to determine a first distance of the reference object relative to the first sensor device; and a second distance sensor in the second housing operable to determine a second distance of the reference object relative to the second sensor device, wherein the first processing unit is operable to calculate the first relative position comprising the first calculated position of the reference object relative to the first sensor device based on:

i) the first image data; and ii) the determined first distance, wherein the second processing unit is operable to calculate the second relative position comprising the second calculated position of the reference object relative to the second sensor device based on:

i) the second image data; and ii) the determined second distance.

3. The medical tracking system according to claim 1, wherein:

the first sensor device comprises a first transmitter configured to transmit the first registration data, and the first relative position comprising the first calculated position of the reference object relative to the first sensor device;

the second sensor device comprises a second transmitter configured to transmit the second registration data, and the second relative position comprising the second calculated position of the reference object relative to the second sensor device;

the control unit is operable to:

receive the first registration data and the first relative position comprising the first calculated position of the reference object relative to the first sensor device from the first transmitter of the first sensor device; and receive the second registration data and the second relative position comprising the second calculated position of the reference object relative to the second sensor device from the second transmitter of the second sensor device.

4. The medical tracking system according to claim 1, wherein:

the first sensor device comprises a transmitter;

the second sensor device comprises a receiver;

the second processing unit comprises the control unit; and the control unit is operable to receive from the transmitter of the first sensor device via the receiver the first registration data and the first relative position comprising the first calculated position of the reference object relative to the first sensor device.

5. The medical tracking system according to claim 1, wherein:

the first processing unit comprises a first part of the control unit; and the second processing unit comprises a second part of the control unit.

6. A medical tracking system for determining a relative position between first and second associated targets, the medical tracking system comprising:

a reference object disposed at a fixed position;

a first independently maneuverable sensor device comprising:

a first housing configured to be rigidly attached with the first associated target;

a first memory device in the first housing the first memory device storing first registration data representative of a relationship between the first sensor device and the first associated target when the first sensor device is rigidly attached with the first associated target;

a first processing unit in the first housing and operatively coupled with the first memory device;

a first transmitter in the first housing and operatively coupled with the first processing unit; and a first camera in the first housing and operatively coupled with the first processing unit, wherein the first camera is operable to generate first image data representative of a first image of the reference object captured by the first camera, wherein the first processing unit is operable to calculate based on the first image data a first relative position comprising a first calculated position of the reference object relative to the first sensor device comprising:

a first spatial location in three translational dimensions between the reference object and the first sensor device; and/or a first alignment in three rotational dimensions between the reference object and the first sensor device; and a second independently maneuverable sensor device comprising:

a second housing different than the first housing, the second housing being configured to be rigidly attached with the second associated target;

a second memory device in the second housing the second memory device storing second registration data representative of a relationship between the second sensor device and the second associated target when the second sensor device is rigidly attached with the second associated target;

a second processing unit in the second housing and operatively coupled with the second memory device;

a first receiver in the second housing and operatively coupled with the second processing unit; and a second camera in the second housing and operatively coupled with the second processing unit, wherein the second camera is operable to generate second image data representative of a second image of the reference object captured by the second camera, wherein the second processing unit is operable to calculate based on the second image data a second relative position comprising a second calculated position of the reference object relative to the second sensor device comprising:

a second spatial location in three translational dimensions between the reference object and the second sensor device; and/or a second alignment in three rotational dimensions between the reference object and the second sensor device, wherein the first sensor device is operable to transmit via the first transmitter, the first registration data and the first relative position comprising the first calculated position of the reference object relative to the first sensor device, wherein the second sensor device is operable to receive via the first receiver, the first registration data and the first relative position comprising the first calculated position of the reference object relative to the first sensor device, wherein the second processing unit is operable in response to: i) the first and second registration data: ii) the first relative position comprising the first calculated position of the reference object relative to the first sensor device; and iii) the second relative position comprising the second calculated position of the reference object relative to the second sensor device, to calculate at least one of:

a third relative position comprising a third calculated position of the first associated target relative to the second associated target; and/or a fourth relative position comprising a fourth calculated position of the second associated target relative to the first associated target.

7. The medical tracking system according to claim 6, wherein:

the first sensor device comprises a second receiver in the first housing and operatively coupled with the first processing unit;

the second sensor device comprises a second transmitter in the second housing and operatively coupled with the second processing unit;

the second transmitter of the second sensor device is operable to transmit the second registration data and the second relative position comprising the second calculated position of the reference object relative to the second sensor device;

the second receiver of the first sensor device is operable to receive the second registration data and the second relative position comprising the second calculated position of the reference object relative to the second sensor device; and the first processing unit of the first sensor device is operable in response to: i) the first relative position comprising the first calculated position of the reference object relative to the first sensor device; ii) the second relative position comprising the second calculated position of the reference object relative to the second sensor device; and iii) one or more of the first registration data and/or the second registration data, to calculate at least one of:

the third relative position comprising the third calculated position of the first associated target relative to the second associated target; and/or the fourth relative position comprising the fourth calculated position of the second associated target relative to the first associated target.

8. The medical tracking system according to claim 6, further comprising:

a first distance sensor in the first housing and operatively coupled with the first processing unit, the first distance sensor being operable to determine a first distance of the reference object relative to the first sensor device; and a second distance sensor in the second housing and operatively coupled with the second processing unit, the second distance sensor being operable to determine a second distance of the reference object relative to the second sensor device, wherein the first processing unit is operable to calculate the first relative position comprising the first calculated position of the reference object relative to the first sensor device based on:

i) the first image data; and ii) the determined first distance, wherein the second processing unit is operable to calculate the second relative position comprising the second calculated position of the reference object relative to the second sensor device based on:

i) the second image data; and ii) the determined second distance.

9. A method in a medical tracking system of determining a relative position between first and second associated targets, the method comprising:

disposing a reference object at a fixed position;

generating first image data by a first camera disposed in a first housing of a first independently maneuverable sensor device of the medical tracking system, the first housing being configured to be rigidly attached with the first associated target during the generating of the first image data, and the first image data being representative of a first image of the reference object captured by the first camera;

storing in a first memory device of the first sensor device first registration data representative of a relationship between the first sensor device and the first associated target when the first sensor device is rigidly attached with the first associated target;

calculating by a first processing unit disposed in the first housing of the first sensor device based on the first image data a first relative position comprising a first calculated position of the reference object relative to the first sensor device comprising:

a first spatial location in three translational dimensions between the reference object and the first sensor device; and/or a first alignment in three rotational dimensions between the reference object and the first sensor device;

generating second image data by a second camera disposed in a second housing of a second independently maneuverable sensor device of the medical tracking system, the second housing being configured to be rigidly attached with the second associated target during the generating of the second image data, and the second image data being representative of a second image of the reference object captured by the second camera;

storing in a second memory device of the second sensor device second registration data representative of a relationship between the second sensor device and the second associated target when the second sensor device is rigidly attached with the second associated target;

calculating by a second processing unit disposed in the second housing of the second sensor device based on the second image data a second relative position comprising a second calculated position of the reference object relative to the second sensor device comprising:

a second spatial location in three translational dimensions between the reference object and the second sensor device; and/or a second alignment in three rotational dimensions between the reference object and the second sensor device; and calculating by a control unit of the medical tracking system at least one of:

a third relative position comprising a third calculated position of the first associated target relative to the second associated target; and/or a fourth relative position comprising a fourth calculated position of the second associated target relative to the first associated target based on: i) the first relative position comprising the first calculated position of the reference object relative to the first sensor device; ii) the second relative position comprising the second calculated position of the reference object relative to the second sensor device; and iii) one or more of the first registration data and/or the second registration data.

10. The method according to claim 9, further comprising:

determining by a first distance sensor disposed in the first housing a first distance of the reference object relative to the first sensor device; and determining by a second distance sensor disposed in the second housing a second distance of the reference object relative to the second sensor device, wherein the first processing unit calculates the first relative position comprising the first calculated position of the reference object relative to the first sensor device based on:

i) the first image data; and ii) the determined first distance, wherein the second processing unit calculates the second relative position comprising the second calculated position of the reference object relative to the second sensor device based on:

i) the second image data; and ii) the determined second distance.

11. The method according to claim 9, further comprising:

transmitting by a first transmitter disposed in the first housing of the first sensor device the first registration data, and the first relative position comprising the first calculated position of the reference object relative to the first sensor device;

transmitting by a second transmitter disposed in the second housing of the second sensor device the second registration data, and the second relative position comprising the second calculated position of the reference object relative to the second sensor device; and receiving the first and second registration data, the first relative position comprising the first calculated position of the reference object relative to the first sensor device, and the second relative position comprising the second calculated position of the reference object relative to the second sensor device by a receiver in operative communication with the control unit of the medical tracking system.

12. The method according to claim 9, further comprising:

transmitting by a transmitter disposed in the first housing of the first sensor device the first registration data and the first relative position comprising the first calculated position of the reference object relative to the first sensor device; and receiving from the transmitter by a receiver disposed in the second sensor device and in operative communication with the control unit the first registration data and the first relative position comprising the first calculated position of the reference object relative to the first sensor device, wherein the second processing unit comprises the control unit.

13. The method according to claim 9, wherein the calculating the third relative position comprising the third calculated position of the first associated target relative to the second associated target comprises:

calculating the first relative position comprising the first calculated position of the reference object relative to the first sensor device based on the first image data by a first part of the control unit disposed in the first housing of the first sensor device; and calculating the second relative position comprising the second calculated position of the reference object relative to the second sensor device based on the second image data by a second part of the control unit disposed in the second housing of the second sensor device, wherein the first processing unit comprises the first part of the control unit, and the second processing unit comprises the second part of the control unit.

14. A method in a medical tracking system of determining a relative position between first and second associated targets, the method comprising:

disposing a reference object at a fixed position;

generating first image data by a first camera disposed in a first housing of a first independently maneuverable sensor device of the medical tracking system, the first housing being configured to be rigidly attached with the first associated target during the generating of the first image data, and the first image data being representative of a first image of the reference object captured by the first camera;

storing in a first memory device of the first sensor device first registration data representative of a relationship between the first sensor device and the first associated target when the first sensor device is rigidly attached with the first associated target;

calculating by a first processing unit disposed in the first housing of the first sensor device based on the first image data a first relative position comprising a first calculated position of the reference object relative to the first sensor device comprising:

a first spatial location in three translational dimensions between the reference object and the first sensor device; and/or a first alignment in three rotational dimensions between the reference object and the first sensor device;

generating second image data by a second camera disposed in a second housing of a second independently maneuverable sensor device of the medical tracking system, the second housing being configured to be rigidly attached with the second associated target during the generating of the second image data, and the second image data being representative of a second image of the reference object captured by the second camera;

storing in a second memory device of the second sensor device second registration data representative of a relationship between the second sensor device and the second associated target when the second sensor device is rigidly attached with the second associated target;

calculating by a second processing unit disposed in the second housing of the second sensor device based on the second image data a second relative position comprising a second calculated position of the reference object relative to the second sensor device comprising:

a second spatial location in three translational dimensions between the reference object and the second sensor device; and/or a second alignment in three rotational dimensions between the reference object and the second sensor device;

transmitting by a transmitter in operative communication with the first processing unit of the first sensor device the first registration data and the first relative position comprising the first calculated position of the reference object relative to the first sensor device;

receiving from the transmitter by a receiver in operative communication with the second processing unit of the second sensor device the first registration data and the first relative position comprising the first calculated position of the reference object relative to the first sensor device; and calculating by the second processing unit at least one of:

a third relative position comprising a third calculated position of the first associated target relative to the second associated target; and/or a fourth relative position comprising a fourth calculated position of the second associated target relative to the first associated target, based on: i) the received first relative position comprising the first calculated position of the reference object relative to the first sensor device; ii) the second relative position comprising the second calculated position of the reference object relative to the second sensor device; and iii) the first and second registration data.

15. The method according to claim 14, further comprising:

transmitting by a second transmitter in operative communication with the second processing unit of the second sensor device the second registration data and the second relative position comprising the second calculated position of the reference object relative to the second sensor device;

receiving from the second transmitter by a second receiver in operative communication with the first processing unit of the first sensor device the second registration data and the second relative position comprising the second calculated position of the reference object relative to the second sensor device; and calculating by the first processing unit at least one of: the third relative position comprising the third calculated position of the first associated target relative to the second associated target; and/or the fourth relative position comprising the fourth calculated position of the second associated target relative to the first associated target based on:

i) the received second relative position comprising the second calculated position of the reference object relative to the second sensor device;

ii) the first relative position comprising the first calculated position of the reference object relative to the first sensor device; and iii) one or more of the first registration data and/or the second registration data.

16. The method according to claim 14, further comprising:

determining by a first distance sensor disposed in the first housing a first distance of the reference object relative to the first sensor device; and determining by a second distance sensor disposed in the second housing a second distance of the reference object relative to the second sensor device, wherein the first processing unit calculates the first relative position comprising the first calculated position of the reference object relative to the first sensor device based on:

i) the first image data; and ii) the determined first distance, wherein the second processing unit calculates the second relative position comprising the second calculated position of the reference object relative to the second sensor device based on:

i) the second image data; and ii) the determined second distance.

17. A medical tracking system for determining a relative position between first and second associated targets, the medical tracking system comprising:

a reference object disposed at a fixed position;

a first independently maneuverable sensor device comprising:

a first housing configured to be rigidly attached with the first associated target;

a first memory device in the first housing, the first memory device storing first registration data representative of a relationship between the first sensor device and the first associated target when the first sensor device is rigidly attached with the first associated target;

a first processing unit in the first housing and operatively coupled with the first memory device; and a first camera mounted relative to the first housing and operatively coupled with the first processing unit, wherein the first camera is operable to generate first image data representative of a first image of the reference object captured by the first camera, wherein the first processing unit is operable to calculate based on the first image data a first relative position comprising a first calculated position of the reference object relative to the first sensor device comprising:

a first spatial location in three translational dimensions between the reference object and the first sensor device; and/or a first alignment in three rotational dimensions between the reference object and the first sensor device;

wherein the first processing unit is operable to calculate a relative position between the first associated target and the reference object based on the first registration data and the first calculated position of the reference object relative to the first sensor device;

a second independently maneuverable sensor device comprising:

a second housing different than the first housing, the second housing being configured to be rigidly attached with the second associated target;

a second memory device in the second housing, the second memory device storing second registration data representative of a relationship between the second sensor device and the second associated target when the second sensor device is rigidly attached with the second associated target;

a second processing unit in the second housing and operatively coupled with the second memory device; and a second camera mounted relative to the second housing and operatively coupled with the second processing unit, wherein the second camera is operable to generate second image data representative of a second image of the reference object captured by the second camera, wherein the second processing unit is operable to calculate based on the second image data a second relative position comprising a second calculated position of the reference object relative to the second sensor device comprising:

a second spatial location in three translational dimensions between the reference object and the second sensor device; and/or a second alignment in three rotational dimensions between the reference object and the second sensor device, wherein the second processing unit is operable to calculate a relative position between the second associated target and the reference object based on the second registration data and the second calculated position of the reference object relative to the second sensor device; and a control unit operable to calculate based on: i) the calculated relative position between the first associated target and the reference object, and ii) the calculated relative position between the second associated target and the reference object, at least one of:

a third relative position comprising a third calculated position of the first associated target relative to the second associated target; and/or a fourth relative position comprising a fourth calculated position of the second associated target relative to the first associated target.

18. The medical tracking system according to claim 17, further comprising:

a first distance sensor operable to determine a first distance between the reference object and the first sensor device; and a second distance sensor operable to determine a second distance between the reference object and the second sensor device, wherein the first processing unit is operable to calculate the first relative position comprising the first calculated position of the reference object relative to the first sensor device based on:

i) the first image data; and ii) the first distance between the reference object and the first sensor device determined by the first distance sensor, wherein the second processing unit is operable to calculate the second relative position comprising the second calculated position of the reference object relative to the second sensor device based on:

i) the second image data; and ii) the second distance between the reference object and the second sensor device determined by the second distance sensor.

19. The medical tracking system according to claim 17, wherein:

the first sensor device comprises a first transmitter configured to transmit data representative of the calculated relative position between the first associated target and the reference object;

the second sensor device comprises a second transmitter configured to transmit data representative of the calculated relative position between the second associated target and the reference object; and the control unit is operable to receive:

the data representative of the calculated relative position between the first associated target and the reference object; and the data representative of the calculated relative position between the second associated target and the reference object.

20. The medical tracking system according to claim 17, wherein:

the first sensor device comprises a transmitter configured to transmit data representative of the calculated relative position between the first associated target and the reference object;

the second sensor device comprises a receiver operable to receive the data representative of the calculated relative position between the first associated target and the reference object; and the second processing unit comprises the control unit.

21. The medical tracking system according to claim 17, wherein:

the first processing unit of the first sensor device comprises a first part of the control unit; and the second processing unit of the second sensor device comprises a second part of the control unit.

22. A medical tracking system for determining a relative position between first and second associated targets, the medical tracking system comprising:

a reference object disposed at a fixed position;

a first independently maneuverable sensor device comprising:

a first housing configured to be rigidly attached with the first associated target;

a first memory device in the first housing, the first memory device storing first registration data representative of a relationship between the first sensor device and the first associated target when the first sensor device is rigidly attached with the first associated target;

a first processing unit in the first housing and operatively coupled with the first memory device;

a first transmitter in the first housing and operatively coupled with the first processing unit; and a first camera mounted relative to the first housing and operatively coupled with the first processing unit, wherein the first camera is operable to generate first image data representative of a first image of the reference object captured by the first camera, wherein the first processing unit is operable to calculate based on the first image data a first relative position comprising a first calculated position of the reference object relative to the first sensor device comprising:

a first spatial location in three translational dimensions between the reference object and the first sensor device; and/or a first alignment in three rotational dimensions between the reference object and the first sensor device, wherein the first processing unit is operable to calculate a relative position between the first associated target and the reference object based on the first registration data and the first calculated position of the reference object relative to the first sensor device; and a second independently maneuverable sensor device comprising:

a second housing different than the first housing, the second housing being configured to be rigidly attached with the second associated target;

a second memory device in the second housing, the second memory device storing second registration data representative of a relationship between the second sensor device and the second associated target when the second sensor device is rigidly attached with the second associated target;

a second processing unit in the second housing and operatively coupled with the second memory device;

a first receiver in the second housing and operatively coupled with the second processing unit; and a second camera mounted relative to the second housing and operatively coupled with the second processing unit, wherein the second camera is operable to generate second image data representative of a second image of the reference object captured by the second camera, wherein the second processing unit is operable to calculate based on the second image data a second relative position comprising a second calculated position of the reference object relative to the second sensor device comprising:

a second spatial location in three translational dimensions between the reference object and the second sensor device; and/or a second alignment in three rotational dimensions between the reference object and the second sensor device, wherein the second processing unit is operable to calculate a relative position between the second associated target and the reference object based on the second registration data and the second calculated position of the reference object relative to the second sensor device;

wherein the first sensor device is operable to transmit via the first transmitter data representative of the calculated relative position between the first associated target and the reference object, wherein the second sensor device is operable to receive via the first receiver the data representative of the calculated relative position between the first associated target and the reference object, wherein the second processing unit is operable in response to: i) the calculated relative position between the first associated target and the reference object; and ii) the calculated relative position between the second associated target and the reference object, to calculate at least one of:

a third relative position comprising a third calculated position of the first associated target relative to the second associated target: and/or a fourth relative position comprising a fourth calculated position of the second associated target relative to the first associated target.

23. The medical tracking system according to claim 22, wherein:

the first sensor device comprises a second receiver in the first housing and operatively coupled with the first processing unit;

the second sensor device comprises a second transmitter in the second housing and operatively coupled with the second processing unit;

the second transmitter of the second sensor device is operable to transmit data representative of the calculated relative position between the second associated target and the reference object;

the second receiver of the first sensor device is operable to receive the data representative of the calculated relative position between the second associated target and the reference object; and the first processing unit of the first sensor device is operable in response to: i) the calculated relative position between the first associated target and the reference object; and ii) the calculated relative position between the second associated target and the reference object, to calculate the at least one of:

the third relative position comprising the third calculated position of the first associated target relative to the second associated target; and/or the fourth relative position comprising the fourth calculated position of the second associated target relative to the first associated target.

24. The medical tracking system according to claim 22, further comprising:

a first distance sensor operatively coupled with the first processing unit, the first distance sensor being operable to determine a first distance between the first sensor device and the reference object; and a second distance sensor operatively coupled with the second processing unit, the second distance sensor being operable to determine a second distance between the second sensor device and the reference object, wherein the first processing unit is operable to calculate the first relative position comprising the first calculated position of the reference object relative to the first sensor device based on:

i) the first image data; and ii) the first distance between the first sensor device and the reference object determined by the first distance sensor, wherein the second processing unit is operable to calculate the second relative position comprising the second calculated position of the reference object relative to the second sensor device based on:

i) the second image data; and ii) the second distance between the second sensor device and the reference object determined by the second distance sensor.

25. A method in a medical tracking system of determining a relative position between first and second associated targets, the method comprising:

disposing a reference object at a fixed position;

generating first image data by a first camera mounted relative to a first housing of a first independently maneuverable sensor device of the medical tracking system, the first housing being configured to be rigidly attached with the first associated target during the generating of the first image data, and the first image data being representative of a first image of the reference object captured by the first camera;

storing in a first memory device of the first sensor device first registration data representative of a relationship between the first sensor device and the first associated target when the first sensor device is rigidly attached with the first associated target;

calculating by a first processing unit disposed in the first housing of the first sensor device based on the first image data a first relative position comprising a first calculated position of the reference object relative to the first sensor device comprising:

a first spatial location in three translational dimensions between the reference object and the first sensor device; and/or a first alignment in three rotational dimensions between the reference object and the first sensor device;

calculating by the first processing unit a relative position between the first associated target and the reference object based on the first registration data and the first calculated position of the reference object relative to the first sensor device;

generating second image data by a second camera mounted relative to a second housing of a second independently maneuverable sensor device of the medical tracking system, the second housing being configured to be rigidly attached with the second associated target during the generating of the second image data, and the second image data being representative of a second image of the reference object captured by the second camera;

storing in a second memory device of the second sensor device second registration data representative of a relationship between the second sensor device and the second associated target when the second sensor device is rigidly attached with the second associated target;

calculating by a second processing unit disposed in the second housing of the second sensor device based on the second image data a second relative position comprising a second calculated position of the reference object relative to the second sensor device comprising:

a second spatial location in three translational dimensions between the reference object and the second sensor device; and/or a second alignment in three rotational dimensions between the reference object and the second sensor device; and calculating by the second processing unit a relative position between the second associated target and the reference object based on the second registration data and the second calculated position of the reference object relative to the second sensor device; and calculating by a control unit of the medical tracking system at least one of:

a third relative position comprising a third calculated position of the first associated target relative to the second associated target; and/or a fourth relative position comprising a fourth calculated position of the second associated target relative to the first associated target based on: i) the calculated relative position between the first associated target and the reference object, and ii) the calculated relative position between the second associated target and the reference object.

26. The method according to claim 25, further comprising: determining by a first distance sensor mounted relative to the first housing a first distance between the reference object and the first sensor device; and determining by a second distance sensor mounted relative to the second housing a second distance between the reference object and the second sensor device, wherein the first processing unit calculates the first relative position comprising the first calculated position of the reference object relative to the first sensor device based on: i) the first image data; and ii) the first distance between the reference object and the first sensor device determined by the first distance sensor, wherein the second processing unit calculates the second relative position comprising the second calculated position of the reference object relative to the second sensor device based on: i) the second image data; and ii) the second distance between the reference object and the second sensor device determined by the second distance sensor.

27. The method according to claim 25, further comprising:

transmitting by a first transmitter disposed in the first housing of the first sensor device data representative of the calculated relative position between the first associated target and the reference object;

transmitting by a second transmitter disposed in the second housing of the second sensor device data representative of the data representative of the calculated relative position between the second associated target and the reference object;

receiving, by the control unit, the data representative of the calculated relative position between the first associated target and the reference object; and receiving, by the control unit, the data representative of the calculated relative position between the second associated target and the reference object.

28. The method according to claim 25, further comprising: transmitting by a transmitter disposed in the first housing of the first sensor device data representative of the calculated relative position between the first associated target and the reference object; and receiving by a receiver disposed in the second sensor device and in operative communication with the control unit the data representative of the calculated relative position between the first associated target and the reference object, wherein the second processing unit comprises the control unit.

29. The method according to claim 25, wherein the calculating the at least one of the third and/or fourth relative positions by the control unit comprises:

calculating the at least one of the third and/or fourth relative positions by one or more portions of the control unit disposed in:

the first sensor device; and/or the second sensor device.

30. A method in a medical tracking system of determining a relative position between first and second associated targets, the method comprising:

disposing a reference object at a fixed position;

generating first image data by a first camera mounted relative to a first housing of a first independently maneuverable sensor device of the medical tracking system, the first housing being configured to be rigidly attached with the first associated target during the generating of the first image data, and the first image data being representative of a first image of the reference object captured by the first camera;

storing in a first memory device of the first sensor device first registration data representative of a relationship between the first sensor device and the first associated target when the first sensor device is rigidly attached with the first associated target;

calculating by a first processing unit disposed in the first housing of the first sensor device based on the first image data a first relative position comprising a first calculated position of the reference object relative to the first sensor device comprising:

a first spatial location in three translational dimensions between the reference object and the first sensor device; and/or a first alignment in three rotational dimensions between the reference object and the first sensor device;

calculating by the first processing unit a relative position between the first associated target and the reference object based on the first registration data and the first calculated position of the reference object relative to the first sensor device;

generating second image data by a second camera mounted relative to a second housing of a second independently maneuverable sensor device of the medical tracking system, the second housing being configured to be rigidly attached with the second associated target during the generating of the second image data, and the second image data being representative of a second image of the reference object captured by the second camera;

storing in a second memory device of the second sensor device second registration data representative of a relationship between the second sensor device and the second associated target when the second sensor device is rigidly attached with the second associated target;

calculating by a second processing unit disposed in the second housing of the second sensor device based on the second image data a second relative position comprising a second calculated position of the reference object relative to the second sensor device comprising:

a second spatial location in three translational dimensions between the reference object and the second sensor device; and/or a second alignment in three rotational dimensions between the reference object and the second sensor device;

calculating by the second processing unit a relative position between the second associated target and the reference object based on the second registration data and the second calculated position of the reference object relative to the second sensor device;

transmitting by a transmitter in operative communication with the first processing unit of the first sensor device data representative of the calculated relative position between the first associated target and the reference object;

receiving from the transmitter by a receiver in operative communication with the second processing unit of the second sensor device the data representative of the calculated relative position between the first associated target and the reference object; and calculating by the second processing unit at least one of:

a third relative position comprising a third calculated position of the first associated target relative to the second associated target; and/or a fourth relative position comprising a fourth calculated position of the second associated target relative to the first associated target, based on:

i) the calculated relative position between the first associated target and the reference object; and ii) the calculated relative position between the second associated target and the reference object.

31. The method according to claim 30, further comprising:

transmitting by a second transmitter in operative communication with the second processing unit of the second sensor device data representative of the calculated relative position between the second associated target and the reference object;

receiving from the second transmitter by a second receiver in operative communication with the first processing unit of the first sensor device the data representative of the calculated relative position between the second associated target and the reference object; and calculating by the first processing unit at least one of: the third relative position comprising the third calculated position of the first associated target relative to the second associated target; and/or the fourth relative position comprising the fourth calculated position of the second associated target relative to the first associated target based on:

i) the calculated relative position between the first associated target and the reference object; and ii) the calculated relative position between the second associated target and the reference object.

32. The method according to claim 30, further comprising:

determining by a first distance sensor a first distance of the reference object relative to the first sensor device; and determining by a second distance sensor a second distance of the reference object relative to the second sensor device, wherein the first processing unit calculates the first relative position comprising the first calculated position of the reference object relative to the first sensor device based on:

i) the first image data; and ii) the first distance between the first sensor device and the reference object determined by the first distance sensor, wherein the second processing unit calculates the second relative position comprising the second calculated position of the reference object relative to the second sensor device based on:

i) the second image data; and ii) the second distance between the second sensor device and the reference object determined by the second distance sensor.

* * * * *